US012458518B2

(12) United States Patent
Ashby et al.

(10) Patent No.: US 12,458,518 B2
(45) Date of Patent: Nov. 4, 2025

(54) MEDICAL DEVICE DELIVERY DEVICES, SYSTEMS, AND METHODS

(71) Applicant: Covidien LP, Mansfield, MA (US)

(72) Inventors: Mark Ashby, Laguna Niguel, CA (US); Danyong Zeng, Aliso Viejo, CA (US); Agee Barooni, Irvine, CA (US); Khoa Dang Vu, Santa Ana, CA (US); Ashok Nageswaran, Irvine, CA (US)

(73) Assignee: COVIDIEN LP, Mansfield, MA (US)

( * ) Notice: Subject to any disclaimer, the term of this patent is extended or adjusted under 35 U.S.C. 154(b) by 1019 days.

(21) Appl. No.: 17/249,010

(22) Filed: Feb. 17, 2021

(65) Prior Publication Data

US 2022/0257396 A1 Aug. 18, 2022

(51) Int. Cl.
*A61F 2/95* (2013.01)

(52) U.S. Cl.
CPC ........ *A61F 2/95* (2013.01); *A61F 2002/9505* (2013.01)

(58) Field of Classification Search
CPC .... A61F 2/95; A61F 2/966; A61F 2002/9505; A61F 2002/9665
See application file for complete search history.

(56) References Cited

U.S. PATENT DOCUMENTS 3,416,531 A 12/1968 Lowell
4,364,391 A 12/1982 Toye
4,425,919 A 1/1984 Alston, Jr. et al.
4,516,972 A 5/1985 Samson
4,723,936 A 2/1988 Buchbinder et al.
4,877,031 A 10/1989 Conway et al.
4,990,151 A 2/1991 Wallsten
5,011,478 A 4/1991 Cope
5,026,377 A 6/1991 Burton et al.
(Continued)

FOREIGN PATENT DOCUMENTS

CN 104582643 A 4/2015
CN 105232195 A 1/2016
(Continued)

OTHER PUBLICATIONS

Search Report dated Mar. 24, 2020, CN Application No. 201880007614.9, 10 pages.
(Continued)

*Primary Examiner* — Katherine M Rodjom
(74) *Attorney, Agent, or Firm* — Fortem IP LLP

(57) ABSTRACT

Medical device delivery devices, systems, and methods are disclosed herein. According to some embodiments, a medical device delivery system includes a core member and a coupling assembly positioned about the core member. The coupling assembly may include an engagement member having projections configured to engage a medical device and a release member that is movable between a compressed configuration and an expanded configuration. A medical device can extend along the core member such that, when the release member is in the compressed configuration, the projections of the engagement member engage the medical device and when the release member is in the expanded configuration, the release member prevents the projections from engaging the medical device and/or facilitates expansion of the medical device.

22 Claims, 8 Drawing Sheets

(56) References Cited

U.S. PATENT DOCUMENTS

| | | | |
|---|---|---|---|
| 5,037,404 | A | 8/1991 | Gold et al. |
| 5,037,427 | A | 8/1991 | Harada et al. |
| 5,061,275 | A | 10/1991 | Wallsten et al. |
| 5,098,393 | A | 3/1992 | Amplatz et al. |
| 5,108,411 | A | 4/1992 | Mckenzie |
| 5,147,370 | A | 9/1992 | Mcnamara et al. |
| 5,178,158 | A | 1/1993 | De Toledo |
| 5,201,316 | A | 4/1993 | Pomeranz et al. |
| 5,209,734 | A | 5/1993 | Hurley et al. |
| 5,279,562 | A | 1/1994 | Sirhan et al. |
| 5,279,596 | A | 1/1994 | Castaneda et al. |
| 5,292,311 | A | 3/1994 | Cope |
| 5,318,032 | A | 6/1994 | Lonsbury et al. |
| 5,318,525 | A | 6/1994 | West et al. |
| 5,318,529 | A | 6/1994 | Kontos |
| 5,358,493 | A | 10/1994 | Schweich, Jr. et al. |
| 5,382,259 | A | 1/1995 | Phelps et al. |
| 5,389,087 | A | 2/1995 | Miraki |
| 5,403,292 | A | 4/1995 | Ju |
| 5,437,288 | A | 8/1995 | Schwartz et al. |
| 5,445,646 | A | 8/1995 | Euteneuer et al. |
| 5,454,795 | A | 10/1995 | Samson |
| 5,458,605 | A | 10/1995 | Klemm |
| 5,474,563 | A | 12/1995 | Myler et al. |
| 5,478,349 | A | 12/1995 | Nicholas |
| 5,484,444 | A | 1/1996 | Braunschweiler et al. |
| 5,496,294 | A | 3/1996 | Hergenrother et al. |
| 5,499,975 | A | 3/1996 | Cope et al. |
| 5,522,822 | A | 6/1996 | Phelps et al. |
| 5,531,721 | A | 7/1996 | Pepin et al. |
| 5,534,007 | A | 7/1996 | St. Germain et al. |
| 5,545,209 | A | 8/1996 | Roberts et al. |
| 5,554,139 | A | 9/1996 | Okajima |
| 5,569,220 | A | 10/1996 | Webster, Jr. |
| 5,571,135 | A | 11/1996 | Fraser et al. |
| 5,573,520 | A | 11/1996 | Schwartz et al. |
| 5,584,821 | A | 12/1996 | Hobbs et al. |
| 5,599,325 | A | 2/1997 | Ju et al. |
| 5,599,326 | A | 2/1997 | Carter |
| 5,601,539 | A | 2/1997 | Corso, Jr. |
| 5,636,641 | A | 6/1997 | Fariabi |
| 5,645,559 | A | 7/1997 | Hachtman et al. |
| 5,658,264 | A | 8/1997 | Samson |
| 5,662,622 | A | 9/1997 | Gore et al. |
| 5,676,659 | A | 10/1997 | Mcgurk |
| 5,695,483 | A | 12/1997 | Samson |
| 5,695,499 | A | 12/1997 | Helgerson et al. |
| 5,702,373 | A | 12/1997 | Samson |
| 5,702,418 | A | 12/1997 | Ravenscroft |
| 5,704,926 | A | 1/1998 | Sutton |
| 5,709,703 | A | 1/1998 | Lukic et al. |
| 5,711,909 | A | 1/1998 | Gore et al. |
| 5,716,410 | A | 2/1998 | Wang et al. |
| 5,725,513 | A | 3/1998 | Ju et al. |
| 5,725,571 | A | 3/1998 | Imbert et al. |
| 5,728,063 | A | 3/1998 | Preissman et al. |
| 5,741,429 | A | 4/1998 | Donadio, III et al. |
| 5,743,876 | A | 4/1998 | Swanson |
| 5,755,777 | A | 5/1998 | Chuter |
| 5,759,173 | A | 6/1998 | Preissman et al. |
| 5,776,141 | A | 7/1998 | Klein et al. |
| 5,782,811 | A | 7/1998 | Samson et al. |
| 5,791,036 | A | 8/1998 | Goodin et al. |
| 5,824,041 | A | 10/1998 | Lenker et al. |
| 5,833,632 | A | 11/1998 | Jacobsen et al. |
| 5,836,925 | A | 11/1998 | Soltesz |
| 5,836,926 | A | 11/1998 | Peterson et al. |
| 5,851,203 | A | 12/1998 | Van Muiden |
| 5,853,400 | A | 12/1998 | Samson |
| 5,873,866 | A | 2/1999 | Kondo et al. |
| 5,876,386 | A | 3/1999 | Samson |
| 5,891,112 | A | 4/1999 | Samson |
| 5,897,529 | A | 4/1999 | Ponzi |
| 5,897,537 | A | 4/1999 | Berg et al. |
| 5,902,290 | A | 5/1999 | Peacock, III et al. |
| 5,906,605 | A | 5/1999 | Coxum |
| 5,935,161 | A | 8/1999 | Robinson et al. |
| 5,938,653 | A | 8/1999 | Pepin |
| 5,951,494 | A | 9/1999 | Wang et al. |
| 5,951,539 | A | 9/1999 | Nita et al. |
| 5,961,510 | A | 10/1999 | Fugoso et al. |
| 5,968,053 | A | 10/1999 | Revelas |
| 5,968,069 | A | 10/1999 | Dusbabek et al. |
| 5,971,975 | A | 10/1999 | Mills et al. |
| 5,984,963 | A | 11/1999 | Ryan et al. |
| 6,017,323 | A | 1/2000 | Chee |
| 6,030,371 | A | 2/2000 | Pursley |
| 6,045,547 | A | 4/2000 | Ren et al. |
| 6,053,903 | A | 4/2000 | Samson |
| 6,053,904 | A | 4/2000 | Scribner et al. |
| 6,077,258 | A | 6/2000 | Lange et al. |
| 6,077,295 | A | 6/2000 | Limon et al. |
| 6,077,297 | A | 6/2000 | Robinson et al. |
| 6,083,152 | A | 7/2000 | Strong |
| 6,093,177 | A | 7/2000 | Javier, Jr. et al. |
| 6,105,651 | A | 8/2000 | Leanna |
| 6,106,510 | A | 8/2000 | Lunn et al. |
| 6,106,540 | A | 8/2000 | Dehdashtian et al. |
| 6,123,723 | A | 9/2000 | Konya et al. |
| 6,126,685 | A | 10/2000 | Lenker et al. |
| 6,135,992 | A | 10/2000 | Wang |
| 6,149,680 | A | 11/2000 | Shelso et al. |
| 6,152,912 | A | 11/2000 | Jansen et al. |
| 6,152,944 | A | 11/2000 | Holman et al. |
| 6,159,219 | A | 12/2000 | Ren |
| 6,165,163 | A | 12/2000 | Chien et al. |
| 6,165,166 | A | 12/2000 | Samuelson et al. |
| 6,171,295 | B1 | 1/2001 | Garabedian et al. |
| 6,171,296 | B1 | 1/2001 | Chow |
| 6,171,297 | B1 | 1/2001 | Pedersen et al. |
| 6,186,986 | B1 | 2/2001 | Berg et al. |
| 6,193,739 | B1 | 2/2001 | Chevillon et al. |
| 6,197,015 | B1 | 3/2001 | Wilson |
| 6,217,565 | B1 | 4/2001 | Cohen |
| 6,217,566 | B1 | 4/2001 | Ju et al. |
| 6,251,132 | B1 | 6/2001 | Ravenscroft et al. |
| 6,258,080 | B1 | 7/2001 | Samson |
| 6,264,683 | B1 | 7/2001 | Stack et al. |
| 6,287,315 | B1 | 9/2001 | Wijeratne et al. |
| 6,325,807 | B1 | 12/2001 | Que |
| 6,350,278 | B1 | 2/2002 | Lenker et al. |
| 6,355,027 | B1 | 3/2002 | Le et al. |
| 6,358,238 | B1 | 3/2002 | Sherry |
| 6,358,460 | B1 | 3/2002 | Hunt, Jr. et al. |
| 6,368,316 | B1 | 4/2002 | Jansen et al. |
| 6,371,953 | B1 | 4/2002 | Beyar et al. |
| 6,383,171 | B1 | 5/2002 | Gifford et al. |
| 6,387,118 | B1 | 5/2002 | Hanson |
| 6,389,087 | B1 | 5/2002 | Heinonen et al. |
| 6,395,008 | B1 | 5/2002 | Ellis et al. |
| 6,395,017 | B1 | 5/2002 | Dwyer et al. |
| 6,398,791 | B1 | 6/2002 | Que et al. |
| 6,419,693 | B1 | 7/2002 | Fariabi |
| 6,425,898 | B1 | 7/2002 | Wilson et al. |
| 6,428,552 | B1 | 8/2002 | Sparks |
| 6,443,971 | B1 | 9/2002 | Boylan et al. |
| 6,458,075 | B1 | 10/2002 | Sugiyama et al. |
| 6,464,684 | B1 | 10/2002 | Galdonik |
| 6,468,298 | B1 | 10/2002 | Pelton |
| 6,475,184 | B1 | 11/2002 | Wang et al. |
| 6,494,907 | B1 | 12/2002 | Bulver |
| 6,508,804 | B2 | 1/2003 | Sarge et al. |
| 6,508,805 | B1 | 1/2003 | Garabedian et al. |
| 6,508,806 | B1 | 1/2003 | Hoste |
| 6,517,547 | B1 | 2/2003 | Feeser et al. |
| 6,554,820 | B1 | 4/2003 | Wendlandt et al. |
| 6,562,021 | B1 | 5/2003 | Derbin et al. |
| 6,562,063 | B1 | 5/2003 | Euteneuer et al. |
| 6,576,006 | B2 | 6/2003 | Limon et al. |
| 6,582,460 | B1 | 6/2003 | Cryer |
| 6,589,227 | B2 | 7/2003 | Soenderskov Klint |
| 6,602,271 | B2 | 8/2003 | Adams et al. |
| 6,607,551 | B1 | 8/2003 | Sullivan et al. |
| 6,622,367 | B1 | 9/2003 | Bolduc et al. |

(56) References Cited

U.S. PATENT DOCUMENTS

| | | | |
|---|---|---|---|
| 6,635,047 | B2 | 10/2003 | Forsberg |
| 6,638,245 | B2 | 10/2003 | Miller et al. |
| 6,641,564 | B1 | 11/2003 | Kraus |
| 6,648,654 | B1 | 11/2003 | Hembree |
| 6,648,874 | B2 | 11/2003 | Parisi et al. |
| 6,652,508 | B2 | 11/2003 | Griffin et al. |
| 6,663,614 | B1 | 12/2003 | Carter |
| 6,669,719 | B2 | 12/2003 | Wallace et al. |
| 6,689,120 | B1 | 2/2004 | Gerdts |
| 6,699,274 | B2 | 3/2004 | Stinson |
| 6,702,782 | B2 | 3/2004 | Miller et al. |
| 6,706,055 | B2 | 3/2004 | Douk et al. |
| 6,716,207 | B2 | 4/2004 | Farnholtz |
| 6,726,659 | B1 | 4/2004 | Stocking et al. |
| 6,764,504 | B2 | 7/2004 | Wang et al. |
| 6,808,529 | B2 | 10/2004 | Fulkerson |
| 6,814,749 | B2 | 11/2004 | Cox et al. |
| 6,815,325 | B2 | 11/2004 | Ishii |
| 6,817,995 | B1 | 11/2004 | Halpern |
| 6,830,575 | B2 | 12/2004 | Stenzel et al. |
| 6,837,890 | B1 | 1/2005 | Chludzinski et al. |
| 6,843,802 | B1 | 1/2005 | Villalobos et al. |
| 6,858,024 | B1 | 2/2005 | Berg et al. |
| 6,866,660 | B2 | 3/2005 | Garabedian et al. |
| 6,866,679 | B2 | 3/2005 | Kusleika |
| 6,932,837 | B2 | 8/2005 | Amplatz et al. |
| 6,939,353 | B2 | 9/2005 | Que et al. |
| 6,945,970 | B2 | 9/2005 | Pepin |
| 6,960,227 | B2 | 11/2005 | Jones et al. |
| 6,984,963 | B2 | 1/2006 | Pidutti et al. |
| 6,989,024 | B2 | 1/2006 | Hebert et al. |
| 7,001,369 | B2 | 2/2006 | Griffin et al. |
| 7,011,675 | B2 | 3/2006 | Hemerick et al. |
| 7,025,758 | B2 | 4/2006 | Klint |
| 7,074,236 | B2 | 7/2006 | Rabkin et al. |
| 7,104,979 | B2 | 9/2006 | Jansen et al. |
| 7,147,656 | B2 | 12/2006 | Andreas et al. |
| 7,156,860 | B2 | 1/2007 | Wallsten |
| 7,163,523 | B2 | 1/2007 | Devens, Jr. et al. |
| 7,166,088 | B2 | 1/2007 | Heuser |
| 7,166,099 | B2 | 1/2007 | Devens, Jr. |
| 7,166,100 | B2 | 1/2007 | Jordan et al. |
| 7,172,575 | B2 | 2/2007 | El-nounou et al. |
| 7,223,263 | B1 | 5/2007 | Seno |
| 7,228,878 | B2 | 6/2007 | Chen et al. |
| 7,306,624 | B2 | 12/2007 | Yodfat et al. |
| 7,323,000 | B2 | 1/2008 | Monstdt et al. |
| 7,331,948 | B2 | 2/2008 | Skarda |
| 7,357,812 | B2 | 4/2008 | Andreas et al. |
| 7,371,248 | B2 | 5/2008 | Dapolito et al. |
| 7,402,151 | B2 | 7/2008 | Rosenman et al. |
| 7,404,820 | B2 | 7/2008 | Mazzocchi et al. |
| 7,427,288 | B2 | 9/2008 | Sater |
| 7,438,712 | B2 | 10/2008 | Chouinard |
| 7,445,684 | B2 | 11/2008 | Pursley |
| 7,473,271 | B2 | 1/2009 | Gunderson |
| 7,473,272 | B2 | 1/2009 | Pryor |
| 7,481,804 | B2 | 1/2009 | Devens, Jr. |
| 7,507,229 | B2 | 3/2009 | Hewitt et al. |
| 7,524,322 | B2 | 4/2009 | Monstdt et al. |
| 7,556,634 | B2 | 7/2009 | Lee et al. |
| 7,556,710 | B2 | 7/2009 | Leeflang et al. |
| 7,569,046 | B2 | 8/2009 | Zhou |
| 7,572,290 | B2 | 8/2009 | Yodfat et al. |
| 7,582,079 | B2 | 9/2009 | Wendlandt et al. |
| 7,597,830 | B2 | 10/2009 | Zhou |
| 7,621,904 | B2 | 11/2009 | Mcferran et al. |
| 7,641,646 | B2 | 1/2010 | Kennedy |
| 7,651,520 | B2 | 1/2010 | Fischell et al. |
| 7,655,031 | B2 | 2/2010 | Tenne et al. |
| 7,674,411 | B2 | 3/2010 | Berg et al. |
| 7,691,138 | B2 | 4/2010 | Stenzel et al. |
| 7,708,704 | B2 | 5/2010 | Mitelberg et al. |
| 7,717,953 | B2 | 5/2010 | Kaplan et al. |
| 7,740,652 | B2 | 6/2010 | Gerdts et al. |
| 7,758,624 | B2 | 7/2010 | Dorn et al. |
| 7,766,820 | B2 | 8/2010 | Core |
| 7,766,896 | B2 | 8/2010 | Kornkven Volk et al. |
| 7,780,646 | B2 | 8/2010 | Farnholtz |
| 7,815,600 | B2 | 10/2010 | Al-Marashi et al. |
| 7,815,608 | B2 | 10/2010 | Schafersman et al. |
| 7,815,628 | B2 | 10/2010 | Devens, Jr. |
| 7,828,790 | B2 | 11/2010 | Griffin |
| 7,867,267 | B2 | 1/2011 | Sullivan et al. |
| 7,879,022 | B2 | 2/2011 | Bonnette et al. |
| 7,935,140 | B2 | 5/2011 | Griffin |
| 7,942,925 | B2 | 5/2011 | Yodfat et al. |
| 7,955,370 | B2 | 6/2011 | Gunderson |
| 7,981,148 | B2 | 7/2011 | Aguilar et al. |
| 7,993,385 | B2 | 8/2011 | Levine et al. |
| 8,025,692 | B2 | 9/2011 | Feeser |
| 8,034,095 | B2 | 10/2011 | Randolph et al. |
| 8,042,720 | B2 | 10/2011 | Shifrin et al. |
| 8,048,104 | B2 | 11/2011 | Monstadt et al. |
| 8,066,754 | B2 | 11/2011 | Malewicz |
| 8,083,791 | B2 | 12/2011 | Kaplan et al. |
| 8,088,140 | B2 | 1/2012 | Ferrera et al. |
| 8,092,508 | B2 | 1/2012 | Leynov et al. |
| 8,109,987 | B2 | 2/2012 | Kaplan et al. |
| 8,133,266 | B2 | 3/2012 | Thomas et al. |
| 8,147,534 | B2 | 4/2012 | Berez et al. |
| 8,187,314 | B2 | 5/2012 | Davis et al. |
| 8,257,432 | B2 | 9/2012 | Kaplan et al. |
| 8,298,276 | B2 | 10/2012 | Ozawa et al. |
| 8,317,850 | B2 | 11/2012 | Kusleika |
| 8,337,543 | B2 | 12/2012 | Jordan et al. |
| 8,366,763 | B2 | 2/2013 | Davis et al. |
| 8,382,818 | B2 | 2/2013 | Davis et al. |
| 8,480,701 | B2 | 7/2013 | Monstadt |
| 8,579,958 | B2 | 11/2013 | Kusleika |
| 8,591,566 | B2 | 11/2013 | Newell et al. |
| 8,597,321 | B2 | 12/2013 | Monstadt et al. |
| 8,636,760 | B2 | 1/2014 | Garcia et al. |
| 8,679,172 | B2 | 3/2014 | Dorn et al. |
| 8,790,387 | B2 | 7/2014 | Nguyen et al. |
| 8,858,613 | B2 | 10/2014 | Cragg et al. |
| 8,968,383 | B1 | 3/2015 | Johnson et al. |
| 9,241,782 | B2 | 1/2016 | Besselink |
| 9,393,141 | B2 | 7/2016 | Gerdts et al. |
| 9,433,520 | B2 | 9/2016 | Longo |
| 9,439,795 | B2 | 9/2016 | Wang et al. |
| 9,474,639 | B2 | 10/2016 | Haggstrom et al. |
| 9,775,733 | B2 | 10/2017 | Johnson et al. |
| 9,782,186 | B2 | 10/2017 | Johnson et al. |
| 9,827,126 | B2 | 11/2017 | Losordo et al. |
| 10,786,377 | B2 | 9/2020 | Nageswaran et al. |
| 10,945,867 | B2 | 3/2021 | Nageswaran et al. |
| 11,071,637 | B2 | 7/2021 | Dawson et al. |
| 11,648,140 | B2 | 5/2023 | Nageswaran et al. |
| 11,944,558 | B2 | 4/2024 | Deen et al. |
| 12,109,137 | B2 | 10/2024 | Deen et al. |
| 2001/0020173 | A1 | 9/2001 | Klumb et al. |
| 2001/0027310 | A1 | 10/2001 | Parisi et al. |
| 2001/0029362 | A1 | 10/2001 | Sirhan et al. |
| 2001/0044591 | A1 | 11/2001 | Stevens et al. |
| 2001/0049547 | A1 | 12/2001 | Moore |
| 2002/0029046 | A1 | 3/2002 | Lorentzen et al. |
| 2002/0045929 | A1 | 4/2002 | Diaz |
| 2002/0049412 | A1 | 4/2002 | Madrid et al. |
| 2002/0072789 | A1 | 6/2002 | Hackett et al. |
| 2002/0107526 | A1 | 8/2002 | Greenberg et al. |
| 2002/0111666 | A1 | 8/2002 | Hart et al. |
| 2002/0138128 | A1 | 9/2002 | Stiger et al. |
| 2002/0156459 | A1 | 10/2002 | Ye et al. |
| 2002/0156460 | A1 | 10/2002 | Ye et al. |
| 2002/0165523 | A1 | 11/2002 | Chin et al. |
| 2002/0188342 | A1 | 12/2002 | Rykhus et al. |
| 2003/0004539 | A1 | 1/2003 | Linder et al. |
| 2003/0009208 | A1 | 1/2003 | Snyder et al. |
| 2003/0050600 | A1 | 3/2003 | Ressemann et al. |
| 2003/0191451 | A1 | 10/2003 | Gilmartin |
| 2003/0212410 | A1 | 11/2003 | Stenzel et al. |
| 2003/0212430 | A1 | 11/2003 | Bose et al. |
| 2004/0024416 | A1 | 2/2004 | Yodfat et al. |

(56) References Cited

U.S. PATENT DOCUMENTS

| | | | |
|---|---|---|---|
| 2004/0092868 | A1 | 5/2004 | Murray |
| 2004/0092879 | A1 | 5/2004 | Kraus et al. |
| 2004/0111095 | A1 | 6/2004 | Gordon et al. |
| 2004/0143239 | A1 | 7/2004 | Zhou et al. |
| 2004/0147903 | A1 | 7/2004 | Latini |
| 2004/0158230 | A1 | 8/2004 | Hunn et al. |
| 2004/0181174 | A2 | 9/2004 | Davis et al. |
| 2004/0193140 | A1 | 9/2004 | Griffin et al. |
| 2004/0193243 | A1 | 9/2004 | Mangiardi et al. |
| 2004/0204749 | A1 | 10/2004 | Gunderson |
| 2004/0220585 | A1 | 11/2004 | Nikolchev et al. |
| 2004/0230285 | A1 | 11/2004 | Gifford et al. |
| 2004/0260271 | A1 | 12/2004 | Huyser et al. |
| 2004/0260384 | A1 | 12/2004 | Allen |
| 2004/0267348 | A1 | 12/2004 | Gunderson et al. |
| 2005/0033403 | A1 | 2/2005 | Ward et al. |
| 2005/0070794 | A1 | 3/2005 | Deal et al. |
| 2005/0090802 | A1 | 4/2005 | Connors et al. |
| 2005/0096724 | A1 | 5/2005 | Stenzel et al. |
| 2005/0119719 | A1 | 6/2005 | Wallace et al. |
| 2005/0125051 | A1 | 6/2005 | Eidenschink et al. |
| 2005/0131449 | A1 | 6/2005 | Salahich et al. |
| 2005/0143773 | A1 | 6/2005 | Abrams et al. |
| 2005/0149160 | A1 | 7/2005 | Mcferran |
| 2005/0182388 | A1 | 8/2005 | Garabedian et al. |
| 2005/0182475 | A1 | 8/2005 | Jen et al. |
| 2005/0228361 | A1 | 10/2005 | Tremaglio |
| 2005/0240254 | A1 | 10/2005 | Austin |
| 2005/0267563 | A1 | 12/2005 | Case et al. |
| 2005/0273149 | A1 | 12/2005 | Tran et al. |
| 2005/0277949 | A1 | 12/2005 | Que et al. |
| 2006/0030835 | A1 | 2/2006 | Sherman et al. |
| 2006/0036309 | A1 | 2/2006 | Hebert et al. |
| 2006/0058865 | A1 | 3/2006 | Case et al. |
| 2006/0064123 | A1 | 3/2006 | Bonnette et al. |
| 2006/0074477 | A1 | 4/2006 | Berthiaume et al. |
| 2006/0089618 | A1 | 4/2006 | Mcferran et al. |
| 2006/0095050 | A1 | 5/2006 | Hartley et al. |
| 2006/0100687 | A1 | 5/2006 | Fahey et al. |
| 2006/0100688 | A1 | 5/2006 | Jordan et al. |
| 2006/0116750 | A1 | 6/2006 | Hebert et al. |
| 2006/0129166 | A1 | 6/2006 | Lavelle |
| 2006/0178698 | A1 | 8/2006 | Mcintyre et al. |
| 2006/0184226 | A1 | 8/2006 | Austin |
| 2006/0212042 | A1 | 9/2006 | Lamport et al. |
| 2006/0217682 | A1 | 9/2006 | Stivland et al. |
| 2006/0235502 | A1 | 10/2006 | Belluche et al. |
| 2006/0271093 | A1 | 11/2006 | Holman et al. |
| 2007/0027520 | A1 | 2/2007 | Sherburne |
| 2007/0043430 | A1 | 2/2007 | Stinson |
| 2007/0049903 | A1 | 3/2007 | Jansen et al. |
| 2007/0078504 | A1 | 4/2007 | Mialhe |
| 2007/0088323 | A1 | 4/2007 | Campbell et al. |
| 2007/0100421 | A1 | 5/2007 | Griffin |
| 2007/0117645 | A1 | 5/2007 | Nakashima |
| 2007/0129706 | A1 | 6/2007 | Katoh et al. |
| 2007/0149927 | A1 | 6/2007 | Itou et al. |
| 2007/0161956 | A1 | 7/2007 | Heuser |
| 2007/0185446 | A1 | 8/2007 | Accisano |
| 2007/0203563 | A1 | 8/2007 | Hebert et al. |
| 2007/0233224 | A1 | 10/2007 | Leynov et al. |
| 2007/0239254 | A1 | 10/2007 | Chia et al. |
| 2007/0239261 | A1 | 10/2007 | Bose et al. |
| 2007/0250039 | A1 | 10/2007 | Lobbins et al. |
| 2007/0250040 | A1 | 10/2007 | Provost et al. |
| 2007/0255255 | A1 | 11/2007 | Shah et al. |
| 2007/0255388 | A1 | 11/2007 | Rudakov et al. |
| 2007/0270779 | A1 | 11/2007 | Jacobs et al. |
| 2007/0299424 | A1 | 12/2007 | Cumming et al. |
| 2007/0299500 | A1 | 12/2007 | Hebert et al. |
| 2007/0299501 | A1 | 12/2007 | Hebert et al. |
| 2007/0299502 | A1 | 12/2007 | Hebert et al. |
| 2008/0009934 | A1 | 1/2008 | Schneider et al. |
| 2008/0015558 | A1 | 1/2008 | Harlan |
| 2008/0015678 | A1 | 1/2008 | Kaplan et al. |
| 2008/0027528 | A1 | 1/2008 | Jagger et al. |
| 2008/0033399 | A1 | 2/2008 | Hunn et al. |
| 2008/0033528 | A1 | 2/2008 | Satasiya et al. |
| 2008/0051705 | A1 | 2/2008 | Von et al. |
| 2008/0051761 | A1 | 2/2008 | Slazas et al. |
| 2008/0071301 | A1 | 3/2008 | Matsuura et al. |
| 2008/0077229 | A1 | 3/2008 | Andreas et al. |
| 2008/0082083 | A1 | 4/2008 | Forde et al. |
| 2008/0091169 | A1 | 4/2008 | Heideman et al. |
| 2008/0097398 | A1 | 4/2008 | Mitelberg et al. |
| 2008/0108974 | A1 | 5/2008 | Yee |
| 2008/0132933 | A1 | 6/2008 | Gerber |
| 2008/0132989 | A1 | 6/2008 | Snow et al. |
| 2008/0140180 | A1 | 6/2008 | Dolan et al. |
| 2008/0147001 | A1 | 6/2008 | Al-Marashi et al. |
| 2008/0147162 | A1 | 6/2008 | Andreas et al. |
| 2008/0177249 | A1 | 7/2008 | Heuser et al. |
| 2008/0188865 | A1 | 8/2008 | Miller et al. |
| 2008/0188928 | A1 | 8/2008 | Salahieh et al. |
| 2008/0221666 | A1 | 9/2008 | Licata et al. |
| 2008/0234660 | A2 | 9/2008 | Cumming et al. |
| 2008/0234795 | A1 | 9/2008 | Snow et al. |
| 2008/0243225 | A1 | 10/2008 | Satasiya et al. |
| 2008/0255541 | A1 | 10/2008 | Hoffman et al. |
| 2008/0255653 | A1 | 10/2008 | Schkolnik |
| 2008/0255654 | A1 | 10/2008 | Hebert et al. |
| 2008/0262471 | A1 | 10/2008 | Warnock |
| 2008/0262472 | A1 | 10/2008 | Lunn et al. |
| 2008/0262592 | A1 | 10/2008 | Jordan et al. |
| 2008/0275426 | A1 | 11/2008 | Holman et al. |
| 2008/0300667 | A1 | 12/2008 | Hebert et al. |
| 2008/0312639 | A1 | 12/2008 | Weber |
| 2009/0012500 | A1 | 1/2009 | Murata et al. |
| 2009/0082609 | A1 | 3/2009 | Condado |
| 2009/0105802 | A1 | 4/2009 | Henry et al. |
| 2009/0125053 | A1 | 5/2009 | Ferrera et al. |
| 2009/0132019 | A1 | 5/2009 | Duffy et al. |
| 2009/0138066 | A1 | 5/2009 | Leopold et al. |
| 2009/0143849 | A1 | 6/2009 | Ozawa et al. |
| 2009/0149835 | A1 | 6/2009 | Velasco et al. |
| 2009/0157048 | A1 | 6/2009 | Sutermeister et al. |
| 2009/0160112 | A1 | 6/2009 | Ostrovsky |
| 2009/0171319 | A1 | 7/2009 | Guo et al. |
| 2009/0204196 | A1 | 8/2009 | Weber |
| 2009/0240235 | A1 | 9/2009 | Murata |
| 2009/0264985 | A1 | 10/2009 | Bruszewski |
| 2009/0287182 | A1 | 11/2009 | Bishop et al. |
| 2009/0287183 | A1 | 11/2009 | Bishop et al. |
| 2009/0287187 | A1 | 11/2009 | Legaspi et al. |
| 2009/0287292 | A1 | 11/2009 | Becking et al. |
| 2009/0299333 | A1 | 12/2009 | Wendlandt et al. |
| 2009/0299449 | A1 | 12/2009 | Styrc |
| 2009/0318947 | A1 | 12/2009 | Garcia et al. |
| 2010/0020354 | A1 | 1/2010 | Ito |
| 2010/0036363 | A1 | 2/2010 | Watanabe et al. |
| 2010/0049293 | A1 | 2/2010 | Zukowski et al. |
| 2010/0049297 | A1 | 2/2010 | Dorn |
| 2010/0057184 | A1 | 3/2010 | Randolph et al. |
| 2010/0057185 | A1 | 3/2010 | Melsheimer et al. |
| 2010/0069852 | A1 | 3/2010 | Kelley |
| 2010/0087913 | A1 | 4/2010 | Rabkin et al. |
| 2010/0094258 | A1 | 4/2010 | Shimogami et al. |
| 2010/0094394 | A1 | 4/2010 | Beach et al. |
| 2010/0094395 | A1 | 4/2010 | Kellett |
| 2010/0100106 | A1 | 4/2010 | Ferrera |
| 2010/0160863 | A1 | 6/2010 | Heuser |
| 2010/0198334 | A1 | 8/2010 | Yodfat et al. |
| 2010/0204770 | A1 | 8/2010 | Mas et al. |
| 2010/0217235 | A1 | 8/2010 | Thorstenson et al. |
| 2010/0256602 | A1 | 10/2010 | Lippert et al. |
| 2010/0256603 | A1 | 10/2010 | Lippert et al. |
| 2010/0262157 | A1 | 10/2010 | Silver et al. |
| 2010/0268243 | A1 | 10/2010 | Parker |
| 2010/0268328 | A1 | 10/2010 | Stiger |
| 2010/0274270 | A1 | 10/2010 | Patel et al. |
| 2010/0298931 | A1 | 11/2010 | Quadri et al. |
| 2010/0331951 | A1 | 12/2010 | Bei et al. |
| 2011/0009943 | A1 | 1/2011 | Paul et al. |
| 2011/0022157 | A1 | 1/2011 | Essinger et al. |

(56) References Cited

U.S. PATENT DOCUMENTS

| | | | | |
|---|---|---|---|---|
| 2011/0029065 | A1 | 2/2011 | Wood et al. | |
| 2011/0034987 | A1 | 2/2011 | Kennedy | |
| 2011/0054586 | A1 | 3/2011 | Mayberry et al. | |
| 2011/0093055 | A1 | 4/2011 | Kujawski | |
| 2011/0098804 | A1 | 4/2011 | Yeung et al. | |
| 2011/0106235 | A1 | 5/2011 | Haverkost et al. | |
| 2011/0112623 | A1 | 5/2011 | Schatz | |
| 2011/0137403 | A1 | 6/2011 | Rasmussen et al. | |
| 2011/0152760 | A1 | 6/2011 | Parker | |
| 2011/0160763 | A1 | 6/2011 | Ferrera et al. | |
| 2011/0178588 | A1 | 7/2011 | Haselby | |
| 2011/0190862 | A1 | 8/2011 | Bashiri et al. | |
| 2011/0190865 | A1 | 8/2011 | Mchugo et al. | |
| 2011/0208292 | A1 | 8/2011 | Von Oepen et al. | |
| 2011/0224650 | A1 | 9/2011 | Itou et al. | |
| 2011/0257720 | A1 | 10/2011 | Peterson et al. | |
| 2011/0288626 | A1 | 11/2011 | Straubinger et al. | |
| 2011/0319904 | A1 | 12/2011 | Hollett et al. | |
| 2012/0029607 | A1 | 2/2012 | Mchugo et al. | |
| 2012/0035700 | A1 | 2/2012 | Leanna et al. | |
| 2012/0053681 | A1 | 3/2012 | Alkhatib et al. | |
| 2012/0059449 | A1 | 3/2012 | Dorn et al. | |
| 2012/0065660 | A1 | 3/2012 | Ferrera et al. | |
| 2012/0116494 | A1 | 5/2012 | Leynov et al. | |
| 2012/0123511 | A1 | 5/2012 | Brown | |
| 2012/0150272 | A1* | 6/2012 | Melsheimer | A61F 2/966 623/1.11 |
| 2012/0226343 | A1 | 9/2012 | Vo et al. | |
| 2012/0253447 | A1 | 10/2012 | Hayasaka et al. | |
| 2012/0316638 | A1 | 12/2012 | Grad et al. | |
| 2013/0085562 | A1 | 4/2013 | Rincon et al. | |
| 2013/0131775 | A1 | 5/2013 | Hadley et al. | |
| 2013/0172925 | A1 | 7/2013 | Garcia et al. | |
| 2013/0172979 | A1 | 7/2013 | Fargahi | |
| 2013/0226276 | A1 | 8/2013 | Newell et al. | |
| 2013/0226278 | A1 | 8/2013 | Newell et al. | |
| 2013/0261730 | A1 | 10/2013 | Bose et al. | |
| 2013/0274618 | A1 | 10/2013 | Hou et al. | |
| 2013/0274855 | A1 | 10/2013 | Stante et al. | |
| 2013/0274859 | A1 | 10/2013 | Argentine | |
| 2013/0282099 | A1 | 10/2013 | Huynh | |
| 2013/0304185 | A1 | 11/2013 | Newell et al. | |
| 2014/0025150 | A1 | 1/2014 | Lim | |
| 2014/0031918 | A1 | 1/2014 | Newell et al. | |
| 2014/0094929 | A1 | 4/2014 | Shin et al. | |
| 2014/0148893 | A1 | 5/2014 | Kusleika | |
| 2014/0171826 | A1 | 6/2014 | Lampropoulos et al. | |
| 2014/0172067 | A1 | 6/2014 | Brown et al. | |
| 2014/0194919 | A1 | 7/2014 | Losordo et al. | |
| 2014/0200648 | A1 | 7/2014 | Newell et al. | |
| 2014/0276541 | A1 | 9/2014 | Ahluwalia et al. | |
| 2014/0277332 | A1 | 9/2014 | Slazas et al. | |
| 2015/0032198 | A1 | 1/2015 | Folk | |
| 2015/0066128 | A1 | 3/2015 | Losordo et al. | |
| 2015/0066129 | A1 | 3/2015 | Nageswaran et al. | |
| 2015/0066130 | A1 | 3/2015 | Haggstrom et al. | |
| 2015/0066131 | A1 | 3/2015 | Luong et al. | |
| 2015/0080937 | A1 | 3/2015 | Davidson | |
| 2015/0133990 | A1 | 5/2015 | Davidson | |
| 2015/0164666 | A1 | 6/2015 | Johnson et al. | |
| 2015/0238336 | A1 | 8/2015 | Johnson et al. | |
| 2016/0113793 | A1 | 4/2016 | Nishigishi | |
| 2016/0206454 | A1 | 7/2016 | Fischell et al. | |
| 2017/0035592 | A1 | 2/2017 | Haggstrom et al. | |
| 2017/0252161 | A1 | 9/2017 | Tran et al. | |
| 2018/0042745 | A1 | 2/2018 | Losordo et al. | |
| 2018/0200092 | A1 | 7/2018 | Nageswaran et al. | |
| 2018/0263799 | A1 | 9/2018 | Elwood et al. | |
| 2018/0311061 | A1* | 11/2018 | Nolan | A61F 2/82 |
| 2019/0151124 | A1 | 5/2019 | Hammersmark et al. | |
| 2019/0314175 | A1* | 10/2019 | Dawson | A61F 2/95 |
| 2019/0314176 | A1 | 10/2019 | Nageswaran et al. | |
| 2019/0314177 | A1 | 10/2019 | Alonso et al. | |
| 2019/0314179 | A1 | 10/2019 | Nageswaran et al. | |
| 2019/0336312 | A1 | 11/2019 | Nageswaran et al. | |
| 2019/0374358 | A1 | 12/2019 | Nageswaran | |
| 2020/0107949 | A1* | 4/2020 | Bashiri | A61F 2/966 |
| 2020/0375769 | A1 | 12/2020 | Nageswaran et al. | |
| 2020/0405517 | A1 | 12/2020 | Barooni | |
| 2021/0196490 | A1 | 7/2021 | Dawson et al. | |
| 2023/0029736 | A1 | 2/2023 | Deen et al. | |
| 2023/0038177 | A1 | 2/2023 | Deen et al. | |

FOREIGN PATENT DOCUMENTS

| | | | |
|---|---|---|---|
| EP | 1344502 | A2 | 9/2003 |
| JP | 2001504016 | A | 3/2001 |
| JP | 2008518717 | A | 6/2008 |
| JP | 2009532115 | A | 9/2009 |
| JP | 2009542357 | A | 12/2009 |
| JP | 2013500777 | A | 1/2013 |
| JP | 2013158647 | A | 8/2013 |
| WO | WO 9719713 | A2 | 6/1997 |
| WO | WO 9820811 | A1 | 5/1998 |
| WO | 2006052642 | A1 | 5/2006 |
| WO | 2007118005 | A1 | 10/2007 |
| WO | WO 2010127838 | A2 | 11/2010 |
| WO | WO 2011076408 | A1 | 6/2011 |
| WO | WO 2011081997 | A1 | 7/2011 |
| WO | WO 2011122444 | A1 | 10/2011 |
| WO | WO 2012158152 | A1 | 11/2012 |
| WO | WO 2014074462 | A2 | 5/2014 |
| WO | 2019199968 | A1 | 10/2019 |
| WO | 2020072268 | A1 | 4/2020 |

OTHER PUBLICATIONS

International Search Report and Written Opinion mailed Oct. 15, 2020, International Application No. PCT/US20/70151, 110 pages.

Stoeckel, Dieter , et al., "Self-expanding nitinol stents: material and design considerations", Sep. 3, 2003, Springer-Verlag, pp. 292-301. (Year: 2003).

International Search Report and Written Opinion mailed May 23, 2022, International Application No. PCT/US2022/012747, 15 pages.

* cited by examiner

MEDICAL DEVICE DELIVERY DEVICES, SYSTEMS, AND METHODS

TECHNICAL FIELD

The present technology relates to medical device delivery devices, systems, and methods.

BACKGROUND

Walls of the vasculature, particularly arterial walls, may develop areas of pathological dilatation called aneurysms that often have thin, weak walls that are prone to rupturing. Aneurysms are generally caused by weakening of the vessel wall due to disease, injury, or a congenital abnormality. Aneurysms occur in different parts of the body, and the most common are abdominal aortic aneurysms and cerebral (e.g., brain) aneurysms in the neurovasculature. When the weakened wall of an aneurysm ruptures, it can result in death, especially if it is a cerebral aneurysm that ruptures.

Aneurysms are generally treated by excluding or at least partially isolating the weakened part of the vessel from the arterial circulation. For example, conventional aneurysm treatments include: (i) surgical clipping, where a metal clip is secured around the base of the aneurysm; (ii) packing the aneurysm with small, flexible wire coils (micro-coils); (iii) using embolic materials to “fill” an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to support the vessel from collapsing. Methods for delivering these intravascular stents are also well known.

Conventional methods of introducing a compressed stent into a vessel and positioning it within an area of stenosis or an aneurysm include percutaneously advancing a distal portion of a guiding catheter through the vascular system of a patient until the distal portion is proximate the stenosis or aneurysm. A second, inner catheter is advanced through the distal region of the guiding catheter. A stent delivery system is then advanced out of the distal region of the guiding catheter into the vessel until the distal portion of the delivery system carrying the compressed stent is positioned at the point of the lesion within the vessel. The compressed stent is then released and expanded so that it supports the vessel at the point of the lesion.

SUMMARY

The subject technology is illustrated, for example, according to various aspects described below, including with reference to FIGS. 1-8. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., Clause 1 or Clause 23. The other clauses can be presented in a similar manner.

1. A medical device delivery system comprising:
 - a core member configured for advancement within a corporeal lumen; and
 - a coupling assembly positioned about the core member, the coupling assembly comprising:
   - an engagement member positioned about the core member, the engagement member including an outer portion having one or more projections separated by recesses, wherein the projections define an outer diameter of the engagement member; and
   - a resilient member positioned about the core member, wherein the resilient member is movable between a first state in which an outer diameter of the resilient member is smaller than the outer diameter of the engagement member and a second state in which the outer diameter of the resilient member is at least as large as the outer diameter of the engagement member.
2. The system of Clause 1, further comprising a medical device extending along the core member such that, when the resilient member is in the first state, the projections of the engagement member extend into one or more pores of the medical device and, when the resilient member is in the second state, the resilient member prevents the projections from extending into the one or more pores.
3. The system of Clause 1 or Clause 2, further comprising an elongate tube defining a lumen therethrough, wherein the coupling assembly is configured to be positioned within the lumen of the elongate tube such that the resilient member assumes the first state.
4. The system of Clause 3, wherein the coupling assembly is configured to be advanced through the lumen of the elongate tube such that the resilient member assumes the second state after exiting the lumen.
5. The system of any one of Clauses 1 to 4, wherein the resilient member is positioned adjacent to the engagement member.
6. The system of any one of Clauses 1 to 5, wherein the resilient member is positioned proximal of the engagement member.
7. The system of any one of Clauses 1 to 6, wherein the resilient member is a first resilient member positioned proximal of the engagement member, the coupling assembly further comprising a second resilient member positioned about the core member and distal of the engagement member.
8. The system of any one of Clauses 1 to 7, wherein the resilient member abuts the engagement member.
9. The system of any one of Clauses 1 to 7, wherein the resilient member is longitudinally spaced apart from the engagement member.
10. The system of any one of Clauses 1 to 9, wherein the engagement member is a first engagement member and the resilient member is a first resilient member, the coupling assembly further comprising a second engagement member positioned about the core member and a second resilient member positioned about the core member.
11. The system of Clause 10, wherein the first resilient member is positioned proximally of the first engagement member and the second resilient member is positioned proximally of the second engagement member.
12. The system of Clause 10 or Clause 11, wherein the first resilient member abuts the first engagement member, the second resilient member abuts the second engagement member, and the first engagement member is longitudinally spaced apart from the second resilient member.
13. The system of any one of Clauses 10 to 12, wherein the coupling assembly further comprises a tubular spacer positioned between the first engagement member and the second resilient member.

14. The system of any one of Clauses 1 to 13, wherein the resilient member is substantially disc-shaped.
15. The system of any one of Clauses 1 to 14, wherein the resilient member comprises an elastomeric material.
16. The system of Clause 15, wherein the elastomeric material has a Shore A hardness of at least 20.
17. The system of Clause 15 or Clause 16, wherein the elastomeric material has a Shore A hardness of less than about 55.
18. The system of any one of Clauses 15 to 17, wherein the elastomeric material comprises a silicone.
19. The system of any one of Clauses 1 to 18, wherein the resilient member has a thickness of between about 0.025 mm to about 1 mm.
20. The system of any one of Clauses 1 to 19, wherein the outer diameter of the engagement member is greater than a thickness of the engagement member.
21. A medical device delivery system comprising:
a core member configured for advancement through a lumen of an elongate tube;
a coupling assembly positioned about the core member, the coupling assembly comprising:
an engagement member positioned about the core member, the engagement member including an outer surface having one or more projections; and
a release member positioned about the core member adjacent to the engagement member; and
a medical device extending along the core member over the coupling assembly,
wherein the medical device and the coupling assembly are configured to be positioned within a lumen of an elongate tube such that the release member is compressed and the one or more projections extend through one or more pores of the medical device, and
wherein the core member is configured to be distally advanced within the lumen of the elongate tube such that, when the release member and the engagement member are positioned out of the lumen of the elongate tube, the release member and at least a portion of the medical device radially expand.
22. The system of Clause 21, wherein, when the release member radially expands, the release member applies a radial force to the medical device to separate the medical device from the one or more projections.
23. The system of Clause 21 or Clause 22, wherein, when the release member is compressed, an outer diameter of the release member is smaller than an outer diameter of the engagement member.
24. The system of any one of Clauses 21 to 23, wherein, when the release member expands, an outer diameter of the release member is greater than or equal to an outer diameter of the engagement member.
25. The system of any one of Clauses 21 to 24, wherein the release member is self-expanding.
26. The system of any one of Clauses 21 to 25, wherein the release member comprises a resilient material.
27. The system of any one of Clauses 21 to 26, wherein the release member comprises a silicone elastomer.
28. The system of any one of Clauses 21 to 27, wherein the release member comprises a proximal end face and a distal end face, and a sidewall therebetween.
29. The system of Clause 28, wherein the distal end face of the release member is positioned adjacent the engagement member.
30. The system of Clause 28 or Clause 29, wherein the distal end face of the release member abuts the engagement member.
31. The system of any one of Clauses 28 to 30, wherein the sidewall is substantially annular.
32. The system of any one of Clauses 21 to 31, further comprising an elongate tube defining a lumen extending therethrough.
33. The system of any one of Clauses 21 to 32, wherein an outer diameter of the engagement member is greater than a thickness of the engagement member.
34. A medical device delivery system comprising:
a core member; and
a coupling assembly carried by the core member, the coupling assembly comprising:
an engagement member positioned about the core member, the engagement member including an outer surface having one or more projections configured to engage a medical device extending along the core member; and
an expandable element located on the core member at a position longitudinally adjacent to the engagement member, the expandable element having a compressed configuration and an expanded configuration, wherein, when the expandable element is in the compressed configuration the one or more projections engage the medical device, and wherein expansion of the expandable element from the compressed configuration to the expanded configuration causes the medical device to disengage from the projections.
35. The system of Clause 34, wherein, when the expandable element is in the compressed configuration, a largest radial dimension of the expandable element is smaller than a largest radial dimension of the engagement member and, when the expandable element is in the expanded configuration, the largest radial dimension of the expandable element is greater than or equal to the largest radial dimension of the engagement member.
36. The system of Clause 34 or Clause 35, wherein expansion of the expandable element causes the expandable element to apply a radially outwardly directed force to the medical device to cause the medical device to disengage from the projections.
37. The system of any one of Clauses 34 to 36, further comprising an elongate tube having a lumen configured to receive the core member, the medical device, and the coupling assembly therethrough.
38. The system of Clause 37, wherein, when the expandable element is positioned within the lumen of the elongate tube, the expandable element assumes the compressed configuration.
39. The system of Clause 37 or Clause 38, wherein, when the expandable element is advanced out of the lumen of the elongate tube, the expandable element assumes the expanded configuration.
40. The system of any one of Clauses 34 to 39, wherein the expandable element comprises a resilient material.
41. The system of any one of Clauses 34 to 40, wherein the expandable element is self-expanding.
42. The system of any one of Clauses 34 to 41, wherein the expandable element comprises an elastomeric disc.
43. The system of any one of Clauses 34 to 42, further comprising the medical device extending along the core member.
44. The system of any one of Clauses 34 to 43, wherein an outer diameter of the engagement member is greater than a thickness of the engagement member.

45. The system of any one of the preceding Clauses, further comprising a pushing element positioned on the core member proximally of the engagement member, wherein the pushing element is configured to apply a distally directed force to the medical device.
46. The system of any one of the preceding Clauses, wherein the coupling assembly comprises a spacer between the pushing element and the engagement member.
47. The system of any one of the preceding Clauses, wherein the spacer comprises a coil.
48. The system of any one of the preceding Clauses, wherein the spacer comprises a tubular element with flexibility-enhancing cuts.
49. The system of any one of the preceding Clauses, wherein the coupling assembly comprises a distal restraint positioned on the core member distal of the engagement member.
50. The system of any one of the preceding Clauses, wherein the engagement member is rotatably coupled to the core member.
51. The system of any one of the preceding Clauses, wherein the engagement member is configured to longitudinally slide with respect to the core member.
52. The system of any one of the preceding Clauses, wherein the engagement member is configured to tilt with respect to the core member.
53. The system of any one of the preceding Clauses, wherein the medical device is a stent.
54. The system of any one of the preceding Clauses, wherein the medical device is a braided stent comprising braided filaments.
55. The system of any one of the preceding Clauses, wherein the medical device is configured to divert blood flow.
56. A method of delivering a medical device within an elongate tube, the method comprising:

positioning a medical device and a core member carrying a coupling assembly including an engagement member having one or more projections and a release member within a lumen of the elongate tube such that an outer diameter of the release member is smaller than an outer diameter of the engagement member and the one or more projections are engaged with at least a portion of the medical device;

moving the core member distally within the lumen of the elongate tube to position the engagement member and the release member distally of the lumen; and by positioning the engagement member and the release member distally of the lumen, causing the release member to radially expand such that the outer diameter of the release member is greater than or equal to the outer diameter of the engagement member and causing at least a portion of the medical device to radially expand such that the medical device disengages from the projections of the engagement member.

57. The method of Clause 56, wherein causing the release member to radially expand causes the release member to prevent or inhibit the medical device from reengaging with the projections of the engagement member.
58. The method of Clause 56 or Clause 57, wherein the release member is self-expanding.
59. The method of any one of Clauses 56 to 58, wherein the engagement member is a distal engagement member and the release member is a distal release member, the coupling assembly including a proximal engagement member and a proximal release member longitudinally spaced apart from the distal engagement member and the distal release member.
60. The method of any one of Clauses 56 to 59, wherein, after moving the core member distally relative to the lumen of the elongate tube such that a portion of the medical device radially expands, a proximal portion of the medical device remains engaged with the proximal engagement member.
61. The method of any one of Clauses 56 to 60, further comprising proximally retracting the core member prior to releasing the proximal portion of the medical device from the lumen of the elongate tube such that the medical device is recaptured within the lumen of the elongate sheath.
62. The method of Clause 61, wherein by proximally retracting the core member, engagement member pulls the medical device proximally within the lumen of the elongate sheath.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1:
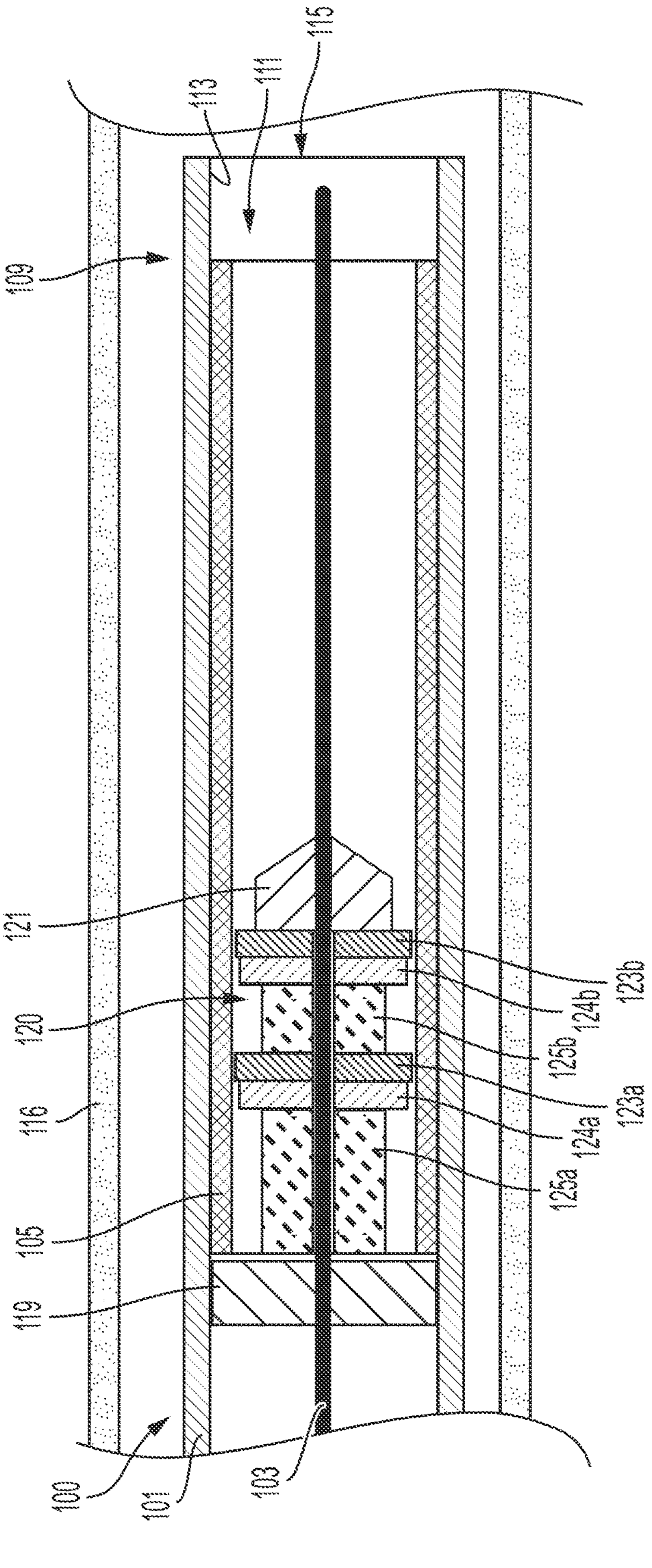
FIG. 1 is a schematic illustration of a medical device delivery system in accordance with several embodiments of the present technology.

Conventional stent engagement members include soft "pads" that rely on friction fit to secure a stent (such as a braided, knit or woven stent, or a laser-cut stent, or other tubular implant or medical device) against an inner wall of a catheter. Such friction-fit pads may require several different pad diameters to accommodate different stent sidewall thicknesses, which can vary based on the wire size (or combinations of wire sizes), or the sidewall thickness of the tube stock, used to form a given stent. That is, within a given catheter size, the internal diameter of the compressed (braided, knit or woven, or laser-cut) stent contained in the catheter will vary based on the sizes (diameters) of the wires, or the wall thickness of the tube stock, and possibly other parameters of the stent corresponding to different deployed sizes or target vessel sizes. This can require using different pad diameters to accommodate different stent sizes within a desired range (e.g. about 3.5 to 5 millimeters in pad diameter), which necessitates manufacturing the pads of various diameters to very small size tolerances.

Other stent engagement members have been developed to address such limitations of conventional stent engagement members and allow a single size stent engagement member to be used with a relatively broad range of stent inner diameters within a given catheter size (e.g. a 0.027", 0.021", or 0.017" inner diameter catheter). Such stent engagement members can comprise a rigid plate, sprocket or member with one or more projections configured to extend into a pore of the stent to engage the stent, for example. However, in some cases one or more portions of the stent can remain engaged with the projections of the stent engagement member as the stent expands. This may be particularly likely when a stent is delivered to a treatment site within a tortuous vessel. When a core member carrying one or more engagement members is curved around a sharp bend in the vessel, the engagement members may be urged toward a side of the vessel opposite the center of curvature of the bend. In this arrangement, even after the stent has been deployed, the engagement members may remain engaged with the stent (e.g., projections of the engagement members may protrude into pores of the stent). Such engagement can prevent the stent from foreshortening and fully radially expanding and/or portions of the stent may be unintentionally drawn into the catheter as the catheter is advanced distally over the stent engagement members to retrieve the stent engagement members after the stent has been deployed. Consequently, multiple manipulations may be required to properly deliver the stent.

The present technology relates to medical device delivery devices, systems, and methods configured to address the above-noted limitations of existing stent engagement members. Some embodiments of the present technology, for example, are directed to a medical device delivery system comprising a coupling assembly including an engagement member configured to engage a medical device and a release member configured to facilitate expansion of the medical device and/or prevent or limit unintentional engagement between the medical device and the engagement member, as may occur following deployment of the stent. Specific details of several embodiments of the technology are described below with reference to FIGS. 1-8. As used herein, the terms "distal" and "proximal" define a position or direction with respect to a clinician or a clinician's control device (e.g., a handle of a delivery catheter). For example, the terms, "distal" and "distally" refer to a position distant from or in a direction away from a clinician or a clinician's control device along the length of device. In a related example, the terms "proximal" and "proximally" refer to a position near or in a direction toward a clinician or a clinician's control device along the length of device.

FIGS. 1-8 depict embodiments of medical device delivery systems that may be used to deliver and/or deploy a medical device, such as but not limited to a stent, into a hollow anatomical structure such as a blood vessel. The stent can comprise a braided stent or other form of stent such as a woven stent, knit stent, laser-cut stent, roll-up stent, etc. The stent can optionally be configured to act as a "flow diverter" device for treatment of aneurysms, such as those found in blood vessels including arteries in the brain or within the cranium, or in other locations in the body such as peripheral arteries. The stent can optionally be similar to any of the versions or sizes of the PIPELINE™ Embolization Device marketed by Medtronic Neurovascular of Irvine, California USA. The stent can alternatively comprise any suitable tubular medical device and/or other features, as described herein. In some embodiments, the stent can be any one of the stents described in U.S. application Ser. No. 15/892,268, filed Feb. 8, 2018, titled VASCULAR EXPANDABLE DEVICES, the entirety of which is hereby incorporated by reference herein and made a part of this specification.

FIG. 1 is a schematic illustration of a medical device delivery system 100 ("system 100") configured in accordance with several embodiments of the present technology. The system 100 can comprise an elongate shaft 101 (e.g., a tube such as a catheter, a microcatheter, sheath, etc.) which is configured to slidably receive a core member or core assembly 103 configured to carry a stent 105 through the elongate shaft 101. As shown in FIG. 1, the elongate shaft 101 can have a proximal region (not shown in FIG. 1) and an opposing distal region 109 which can be positioned at a treatment site within a patient, an internal lumen 111 extending from the proximal region to the distal region 109, and an inner surface 113 defining the lumen 111. At the distal region 109, the elongate shaft 101 has a distal opening 115 through which the core member 103 may be advanced beyond the distal region 109 to expand or deploy the stent 105 within a blood vessel 116. The proximal region may include a catheter hub (not shown). The elongate shaft 101 can define a generally longitudinal dimension extending between the proximal region and the distal region 109. When the delivery system 100 is in use, the longitudinal dimension need not be straight along some or any of its length.

The core member 103 may be configured to extend generally longitudinally through the lumen 111 of the elongate shaft 101. The core member 103 can generally comprise any member(s) with sufficient flexibility and column strength to move the stent 105 or other medical device through the elongate shaft 101. The core member 103 can comprise a wire, tube (e.g., hypotube), braid, coil, or other suitable member(s), or a combination of wire(s), tube(s), braid(s), coil(s), etc.

The system 100 can also include a coupling assembly 120 configured to releasably retain the medical device or stent 105 with respect to the core member 103. The coupling assembly 120 can be configured to engage the stent 105 via mechanical interlock with the pores and filaments of the stent 105, abutment of the proximal end or edge of the stent 105, frictional engagement with the inner wall of the stent 105, or any combination of these modes of action. The coupling assembly 120 can, in some embodiments, cooperate with the overlying inner surface 113 of the elongate shaft 101 to grip and/or abut the stent 105 such that the coupling assembly 120 can move the stent 105 along and within the elongate shaft 101, e.g., distal and/or proximal movement of the core member 103 relative to the elongate shaft 101 results in a corresponding distal and/or proximal movement of the stent 105 within the elongate shaft lumen 111.

The coupling assembly 120 (or portion(s) thereof) can be configured to rotate about the core member 103. In some such embodiments, the coupling assembly 120 comprises a proximal restraint 119 and/or a distal restraint 121. The proximal and distal restraints 119, 121 can be fixed to the core member 103 to prevent or limit proximal or distal movement of the coupling assembly 120 along the longitudinal dimension of the core member 103. For example, the proximal and distal restraints 119, 121 can be soldered, welded, or fixed with adhesive to the core member 103. One or both of the proximal and distal restraints 119, 121 can have an outside diameter or other radially outermost dimension that is smaller than the outside diameter or other radially outermost dimension of the overall coupling assembly 120 such that one or both of the restraints 119, 121 do not apply radial force to the inner surface of the stent 105 during operation of the system 100. In some embodiments, as described in further detail below, the proximal restraint 119 can be sized to abut the proximal end of the stent 105 and be employed to push the stent 105 distally during delivery. As shown in FIG. 1, the distal restraint 121 can taper in the distal direction down towards the core member 103. This tapering can reduce the risk of the distal restraint 121 contacting an inner surface of the stent 105, particularly during navigation of tortuous vasculature, in which the system 100 can assume a highly curved configuration.

The coupling assembly 120 can also include one or more engagement members 123, release members 124, and/or spacers 125 disposed about the core member 103 between the proximal and distal restraints 119, 121. For example, as shown in FIG. 1, the coupling assembly 120 can include first and second engagement members 123*a*, 123*b*, first and second release members 124*a*, 124*b*, and/or first and second spacers 125*a*, 125*b*. In some embodiments (see FIG. 1), from proximal to distal, the elements of the coupling assembly 120 include the proximal restraint 119, followed by the first spacer 125*a*, the first release member 124*a*, the first engagement member 123*a*, the second spacer 125*b*, the second release member 124*b*, the second engagement member 123*b*, and the distal restraint 121. In this configuration, the first spacer 125*a* defines the relative longitudinal spacing between the first release member 124*a* and the proximal restraint 119 and the second spacer 125*b* defines the relative longitudinal spacing between the first engagement member 123*a* and the second release member 124*b*.

One or both of the spacers 125 can take the form of a wire coil, a solid tube, or other structural element that can be mounted over the core member 103 to longitudinally separate adjacent components of the coupling assembly 120. For example, the first spacer 125*a* can have a longitudinal length to separate the proximal restraint 119 from the first release member 124*a* by a desired amount. Additionally or alternatively, the second spacer 125*b* can be configured to have a longitudinal length to separate the first engagement member 123*a* and the second release member 124*b* by a desired amount. For example, in at least some embodiments, the second spacer 125*b* can have a length such that the first engagement member 123*a* is separated from the second engagement member 123*b* by approximately 1-3 times the pore pitch of the overlying stent 105, for example in some embodiments approximately equal to the pore length of the overlying stent 105.

In some embodiments, one or both of the spacers 125 is a zero-pitch coil with flattened ends. For example, the spacer(s) can be a zero-pitch coil configured such that, in an unconstrained condition, each winding of the coil is in direct contact with an adjacent winding of the coil. In such embodiments, the coil can be substantially incompressible along an axial direction under the forces typically encountered during use of the delivery system 100. This incompressibility can provide the pushability of a solid tube spacer while also permitting the bending flexibility of a coil. During bending of the coil, one or more of the windings of the coil may become partially separated from one another to accommodate the bending movement. In the absence of external forces, the coil can return to its unconstrained state (e.g., having zero pitch). In some embodiments, one or both of the spacers 125 is a solid tube (e.g., a laser-cut tube). The tube can be rigid to reduce lateral bending of the delivery system 100. For example, the first spacer 125*a* can comprise a rigid tube to facilitate proper contact between the proximal restraint 119 and the proximal edge or end of the stent 105 during delivery to prevent push forces from concentrating along only a portion of the circumference of the stent 105 and/or slippage of the stent 105 into the radial gap between the outer edge of the proximal restraint 119 and the inner wall 113 of the elongate shaft 101. In some embodiments, one or more of the spacers(s) 125 comprises a tube with one or more flexibility-enhancing cuts (e.g., spiral cuts, periodic arcuate cuts, etc.) configured to enhance the bending flexibility of the spacer(s) 125. In some embodiments, one or more of the spacers 125 can have one or more portions formed from a tube and one or more coil portions. For example, the first spacer 125 can comprise a proximal portion formed from a solid tube and a distal portion formed from a coil.

The spacer(s) 125 can have a proximal end face and a distal end face that are each planar and substantially orthogonal to a longitudinal axis of the spacer 125. For example, in some embodiments the end faces can be ground, polished, or otherwise flattened. This can improve the pushability or column strength of the overall system 100 as the planar surface increases the contact area between the end faces of the spacer 125 and adjacent structures (e.g., the proximal restraint 119, the engagement member 123, the release member 124, etc.). One or both of the spacers 125 can be rotatably mounted or non-rotatably fixed (e.g., soldered) to the core member 103. For example, the spacer 125 can define a central lumen configured to receive the core member 103 therethrough. A radial dimension of the lumen can be greater than a radial dimension of the core member 103 such that the spacer 125 can rotate about the core member. The spacer(s) 125 can have a radially outermost dimension that is smaller than a radially outermost dimension of the engagement members 123 and/or the release members 124 such that the spacers 125 do not apply radial force to the stent 105 during normal operation of the system 100. The dimensions, construction, and configuration of the spacers 125 can be selected to achieve improved grip between the coupling assembly 120 and the overlying stent 105.

In some embodiments, the spacers(s) 125 can be coated with a lubricious material, for example PTFE, parylene, or other coating. The coating can be provided along an outer surface of the spacer 125, within an interior lumen of the spacer 125, or both. In some embodiments, the lubricious coating improves the rotatability of the spacer 125 with respect to the core member 103 and can also reduce friction between the spacer 125 and the overlying stent 105 or elongate sheath 101 in the event that the spacer 125 contacts these components during use of the delivery system 100.

In some embodiments, the second spacer 125*b* can be configured similarly to the first spacer 125*a*. For example, both the first spacer 125*a* and the second spacer 125*b* can be a zero-pitch coil rotatably mounted over the core member 103. In some embodiments, the second spacer 125*b* is configured differently from the first spacer 125*a*. For example, the second spacer 125*b* can be a solid tubular member while the first spacer 125*a* is a zero-pitch coil. The spacers 125 can have the same length or different lengths.

Although FIG. 1 depicts two spacers 125, the coupling assembly 120 can include zero, one, two, or more spacers 125. In some embodiments, multiple spacers 125 can be positioned adjacent to one another such that an end face of one spacer 125 abuts an end face of another spacer 125.

One or both of the engagement members 123 can be a rigid plate, sprocket or member with an aperture configured to receive the core member 103 therethrough. The engagement members 123 may be configured to mechanically interlock with or engage the stent 105 such that the engagement members 123 restrain the stent 105 from moving longitudinally with respect to the core member 103. For example, as described herein, the engagement members 123 can comprise projections configured to extend into pores of the stent 105 when the stent 105 and coupling assembly 120 are positioned within the lumen 111 of the elongate shaft 101.

The coupling assembly 120 can include one or more release members 124 configured to facilitate expansion of the stent 105. As described in more detail herein, the release members 124 can be movable between a first configuration in which the release members 124 permit the engagement members 123 to engage the stent 105 and a second configuration in which the release members 124 inhibit or prevent the engagement members 123 from engaging the stent 105 and/or apply a radial force to the stent 105 to facilitate stent 105 expansion. In some embodiments, when one of the release members 124 is in the first configuration, a radially largest dimension of the release member 124 (e.g., an outer diameter) is smaller than (or no larger than) a radially largest dimension of one or more of the engagement members 123 (shown schematically in FIG. 1). When the release member 124 is in the second configuration, the release member 124 can radially expand so that the radially largest dimension of the release member 124 is greater than or equal to the radially largest dimension of the one or more of the engagement members 123 such that the release member prevents projections of the one or more engagement members from extending into one or more pores of the stent.

For example, some or all of the release members 124 can be resilient (e.g., compressible and self-expandable) and/or elastic or compressible members (e.g., at least partially made of an elastomeric material) that can be compressed, and/or bent or longitudinally or radially deflected, into the first configuration by the overlying elongate shaft 101, stent 105, and/or any other constraining element. In this configuration, the release members 124 permit the engagement members 123 to mechanically interlock with pores of the stent 105. Once released from the elongate shaft 101 (or other constraining element), the release members 124 can return to an uncompressed and/or expanded state (e.g., by self-expansion) to assume the second configuration with a larger radial dimension. In this configuration, the release members 124 can urge the stent 105 away from the engagement members 123 and/or prevent the engagement members 123 from interlocking with pores of the stent. In the illustrated embodiment of FIG. 1, each of the release members 124 are disposed immediately proximal of its respective engagement member 123 (i.e., the first release member **124*a* is disposed proximal of the first engagement member 123*a* and the second release member 124*b* is disposed proximal of the second engagement member 123*b*). In various embodiments, the release members 124 can be positioned proximal of, distal of, or both proximal of and distal of a corresponding engagement member 123. Additionally or alternatively, in some embodiments the number of engagement members 123 and release members 124 need not correspond. For example, a coupling assembly 120 may include a single release member 124 and a plurality of engagement members 123, or conversely may include a single engagement member 123 and a plurality of release members 124. Moreover, although the release members 124 are illustrated as being immediately adjacent and/or in direct contact with corresponding engagement members 123, in some embodiments the release members 124 can be longitudinally spaced apart from the engagement members 123 and/or any spacers 125. For example, some or all of the release members 124 can be separated from an adjacent engagement member 123 and/or spacer 125** by a longitudinal gap.

Although the embodiment illustrated in FIG. 1 includes two engagement members 123, two release members 124, and two spacers 125, other numbers of engagement members 123, release members 124, and spacers 125 are possible. The number of engagement members 123, the number of release members 124, and the number of spacers 125 can be the same or can vary. The number of engagement members 123, the number of release members 124, and/or the number of spacers 125 can be one, two, three, four, five, six, or more. In some embodiments, the coupling assembly 120 does not include an engagement member 123, a release member 124, and/or a spacer 125. For example, the coupling assembly 120 can include a single engagement member 123 and a single release member 124 without any spacers 125.

In some embodiments, for example as shown in FIG. 1, the proximal restraint 119 is configured to abut the proximal end or proximal edge of the stent 105. In this arrangement the proximal restraint 119 can be used to move (e.g., push) the stent 105 distally through the elongate shaft 101 in response to a distal push force applied to the core member 103. Such a proximal restraint 119 can have a diameter that is slightly smaller than the inner diameter of the elongate shaft 101, leaving a radial gap between an outer edge of the proximal restraint 119 and the inner wall 113 of the elongate shaft 101. Additionally or alternatively, the length of the proximal-most spacer 125 (e.g., first spacer **125*a*) can be sized so that the proximal edge of the stent 105 abuts the distal face of the proximal restraint 119**.

When the proximal restraint 119 is configured to push the stent 105 distally, the proximal restraint can be configured to transmit some, most or all of a distally directed longitudinal (e.g., push) force to the stent 105, wholly or partially in place of the engagement members 123. In such a configuration, the engagement members 123 can be configured to transmit little or no push force to the stent 105 while the stent 105 is delivered distally along the length of the elongate shaft 101. Advantageously, this can reduce or eliminate a tendency of the engagement members 123 to distort the pores of the stent 105 with which the engagement members 123 are engaged, when the engagement members 123 are employed to transmit force to and move the stent 105 within the elongate shaft 101. Use of the proximal restraint 119 to move the stent 105 in this manner can also reduce or eliminate longitudinal movement of the stent 105 relative to the core member 103 that sometimes accompanies the pore distortion described above. In most cases, the vast majority of the travel of the stent 105 within the elongate shaft 101 is in the distal or "push" direction during delivery to the treatment location, in contrast to the relatively short travel involved in resheathing the stent 105, in the proximal or "pull" direction, prior to an eventual final deployment of the stent. Therefore, configuring the proximal restraint 119 to transmit most or all of the push force to the stent 105 can significantly reduce or substantially eliminate such distortion and/or relative longitudinal movement of the stent.

The coupling assembly 120 can employ the proximal restraint 119 as a pushing element to transmit at least some, or most or all, distally directed push force to the stent 105 during delivery. In such a coupling assembly 120, the engagement members 123 do not transmit any distally directed push force to the stent 105 during delivery (or transmit only a small portion of such force, or do so only intermittently). The engagement members 123 can transmit proximally directed pull force to the stent 105 during retraction or resheathing, and the proximal restraint 119 can transmit no proximally-directed pull force to the stent (or it may do so occasionally or intermittently, for example when a portion of the stent 105 becomes trapped between the outer edge of the proximal restraint 119 and the inner wall of the elongate shaft 101).

In some embodiments, the engagement members 123 are employed for both distal and proximal movement of the stent 105 with respect to the elongate shaft 101. The engagement members 123 can transmit distally directed force to the stent 105 to move it distally within the elongate shaft 101 during delivery, and proximally directed force to the stent 105 to move it proximally into the elongate shaft 101 during resheathing. In such embodiments, the proximal restraint 119 can be made with a relatively small outer diameter, and/or be positioned sufficiently proximal of the proximal end of the stent 105, to prevent the proximal restraint 119 from transmitting distally directed push forces to the stent 105 during delivery.

In operation, the stent 105 can be moved distally or proximally within the elongate shaft 101 via the core member 103 and the coupling assembly 120. To move the stent 105 out of the elongate shaft 101, the core member 103 is moved distally while the elongate shaft 101 is held stationary, the core member 103 is held stationary while the elongate shaft 101 is withdrawn proximally, or the core member 103 is moved distally while the elongate shaft 101 is simultaneously withdrawn proximally. When the core member 103 is moved distally, the distal face of the proximal restraint 119 bears against the proximal end or edge of the stent 105 and causes the stent to be advanced distally, and ultimately out of the distal region 109 of the elongate shaft 101. In embodiments in which the engagement members 123 are employed to transmit pushing force to the stent 105, the mechanical engagement or interlock between the engagement members 123 and the stent 105, in response to the application of a distally directed force to the core member 103, causes the stent 105 to move distally through and out of the elongate shaft 101. Conversely, to resheath or otherwise move the stent 105 into the elongate shaft 101, the relative movement between the core member 103 and the elongate shaft 101 is reversed compared to moving the stent 105 out of the elongate shaft 101 such that the proximal region of the distal restraint 121 bears against the distal region of the second spacer 125*b* and thereby causes the spacers 125, the release members 124, and the engagement members 123 to be retracted into the lumen 111 of the elongate shaft 101. The mechanical engagement between the engagement members 123 and the stent 105 while the engagement members 123 are positioned within the lumen 111 holds the stent 105 with respect to the core member 103 such that proximal movement of the stent 105 relative to the elongate shaft 101 enables re-sheathing of the stent 105 back into the distal region 109 of the elongate shaft 101. This is useful when the stent 105 has been partially deployed and a portion of the stent 105 remains disposed between at least one of the engagement members 123 (e.g. the first engagement member 123*a*) and the inner surface 113 of the elongate shaft 101 because the stent 105 can be withdrawn back into the distal opening 115 of the elongate shaft 101 by moving the core member 103 proximally relative to the elongate shaft 101 (and/or moving the elongate shaft 101 distally relative to the core member 103). Resheathing in this manner remains possible until the engagement members 123 and/or elongate shaft 101 have been moved to a point where the first engagement member 123*a* is beyond the distal opening 115 of the elongate shaft 101 and the stent 105 is released from between the first engagement member 123*a* and the elongate shaft 101.

The release members 124 are configured to facilitate expansion of the stent 105 as the stent 105 is moved distally out of the lumen 111 of the elongate shaft 101 (e.g., as the elongate shaft 101 is retracted proximally with respect to the coupling assembly 120 and the stent 105). When the stent 105 and coupling assembly 120 are positioned within the lumen 111 of the elongate shaft 101, the stent 105 is radially compressed over the coupling assembly 120. Radial compression (and/or bending or longitudinal deflection) of the release members 124 by the stent 105 and the elongate shaft 101 causes the release members 124 to assume a compressed configuration, enabling the engagement members 123 to engage the stent 105 (e.g., by the projections of the engagement members 123 extending into pores of the stent 105). To deliver the stent 105, the stent 105 and coupling assembly 120 are advanced distally within the lumen 111 of the elongate shaft 101. The elongate shaft 101 can be proximally retracted (and/or the coupling assembly 120 and stent 105 can be distally advanced beyond the distal end of the elongate shaft 101). As the stent 105 begins to extend distally out of the lumen 111 of the elongate shaft 101, the portions of the stent 105 positioned distal of the elongate shaft 101 radially expand. Similarly, once each release member 124 is positioned distal of the elongate shaft 101, the release member 124 radially expands. Accordingly, the release member 124 can be configured to apply a radially outwardly directed force to the stent 105 to facilitate expansion of the stent 105. If a portion of the stent 105 would otherwise remain engaged with the engagement members 123 upon release of the portion of the stent 105 from the elongate shaft 101, the force (e.g., a radial force) applied by the release member 124 to the stent 105 ensures that the portion of the stent 105 disengages from the engagement members 123.

Some or all of the engagement members 123, the release members 124, and/or and the spacers 125 (or any of the engagement members, release members, or spacers disclosed herein) can be fixed to the core member 103 so as to be immovable relative to the core member 103, in a longitudinal/sliding manner and/or in a radial/rotational manner. Alternatively, some or all of the engagement members 123, the release members 124, and/or and the spacers 125 can be coupled to (e.g., mounted on) the core member 103 so that the engagement members 123, the release members 124, and/or and the spacers 125 can rotate about the longitudinal axis of the core member 103, and/or move or slide longitudinally along the core member 103. In such embodiments, the engagement members 123, the release members 124, and/or and the spacers 125 can each have an inner lumen or aperture that receives the core member 103 therein such that the engagement members 123, the release members 124, and/or and the spacers 125 can slide and/or rotate relative to the core member 103. Additionally, in such embodiments, the proximal and distal restraints 119, 121 can be spaced apart along the core member 103 by a longitudinal distance that is slightly greater than the combined length of the engagement members 123, the release members 124, and/or and the spacers 125, so as to leave one or more longitudinal gaps between the spacers 125, the release members 124, and/or the engagement members 123. When present, the longitudinal gap(s) allow the engagement members 123, the release members 124, and/or and the spacers 125 to slide longitudinally along the core member 103 between the restraints 119, 121. The longitudinal range of motion of the engagement members 123, the release members 124, and/or and the spacers 125 between the restraints 119, 121 is approximately equal to the total combined length of the longitudinal gap(s), if any.

Instead of or in addition to the longitudinal gap(s), the coupling assembly 120 can include radial gaps between the outer surface of the core member 103 and the inner surface of the engagement members 123, the release members 124, and/or and the spacers 125. Such radial gaps can be formed when the engagement members 123, the release members 124, and/or and the spacers 125 are constructed with holes that are somewhat larger than the outer diameter of the corresponding portion of the core member 103. When present, the radial gaps allow the engagement members 123, the release members 124, and/or and the spacers 125 to rotate about the longitudinal axis of the core member 103 between the restraints 119, 121. The presence of longitudinal gaps of at least a minimal size on either side of the engagement members 123, the release members 124, and/or and the spacers 125 can also facilitate the rotatability of the components. In various embodiments, the presence and/or size of the radial gaps between the outer surface of the core member 103 and the inner surface of the release members 124 can be based, at least in part, on a desired stability and/or rotatability of the release members 124. For example, the release members 124 can be positioned over the core member 103 with an interference fit. Such interference fit may increase stability of the release members 124 on the core member 103. In some embodiments, for example embodiments in which the release members 124 comprise a silicone elastomer and/or the core member 103 comprises stainless steel, friction between the release members 124 and core member 103 may create negligible and/or small resistance to rotation of the release members 124 about the core member 103. However, such interference fit may increase the difficulty of positioning the release members 124 on the core member 103 in a desired position. In some embodiments, a larger radial gap can facilitate positioning the release members 124 on the core member 103 but may reduce a stability of the release members 124.

In some embodiments, the engagement members 123 and/or the release members 124 can be mounted onto the core member 103 to permit not only rotational movement but also a degree of tilting with respect to a longitudinal axis of the core member 103. For example, the holes in the engagement members 123 and/or the release members 124 can be larger than the outer diameter of the corresponding portion of the core member 103, thereby permitting both rotational movement and tilting with respect to the core member 103. “Tilting” as used herein means that the long axis of the engagement member 123 or release member 124 (e.g., an axis extending along the longest dimension of the engagement member 123 or release member 124, substantially parallel to the proximal-facing and distal-facing end faces of the engagement member 123 or release member 124) is non-orthogonal to a longitudinal axis of the core member 103. For example, in one tilted configuration, the long axis of the first engagement member 123*a* can intersect the core member 103 at approximately 85 degrees, indicating 5 degrees of tilt. Depending on the dimensions of the engagement members 123 or release members 124 and the core member 103, the degree of tilting permitted can vary. In some embodiments, one or both of the engagement members 123 and/or one or both of the or release members 124 can tilt with respect to the core member 103 by 30 degrees or less, 20 degrees or less, 10 degrees or less, or 5 degrees or less. In some embodiments, one or both of the engagement members 123 or one or both of the release members 124 can tilt with respect to the core member 103 by at least 5 degrees, by at least 10 degrees, by at least 20 degrees, or more.

By permitting one or both of the engagement members 123 and/or one or both of the release members 124 to tilt with respect to the core member 103, the coupling assembly 120 can better navigate tortuous anatomy in which the delivery system 100 assumes highly curved states. Additionally, the engagement members 123 or release members 124 can facilitate resheathability of the overlying stent 105 from a partially deployed state. For example, a stent 105 can be in a partially deployed state when a portion of the stent 105 has been moved distally beyond the distal end 115 of the elongate shaft 101 such that the stent 105 has been released from the second engagement member 123*b* yet the stent 105 remains engaged with the first engagement member 123*a*. From this partially deployed state, the stent 105 can be resheathed or recaptured by distally advancing the elongate shaft 101 with respect to the coupling assembly 120 (or, alternatively, by proximally retracting the core member 103 and coupling assembly 120 with respect to the elongate shaft 101). During this movement, as the stent 105 moves proximally with respect to the elongate shaft 101, the stent 105 begins to collapse along its length until it assumes an outer diameter corresponding to the inner diameter of the elongate shaft 101. As the stent 105 is radially compressed, the second release member 124*b* is also radially compressed so that the stent 105 engages the second engagement member 123*b*. With continued distal movement of the elongate shaft 101 with respect to the coupling assembly 120, the second engagement member 123*b* and the second release member 124*b* are eventually received within the lumen 111 of the elongate shaft 101, with the stent 105 interlocked with the second engagement member 123*b* and held in that relationship by the elongate shaft 101.

Figure 2:
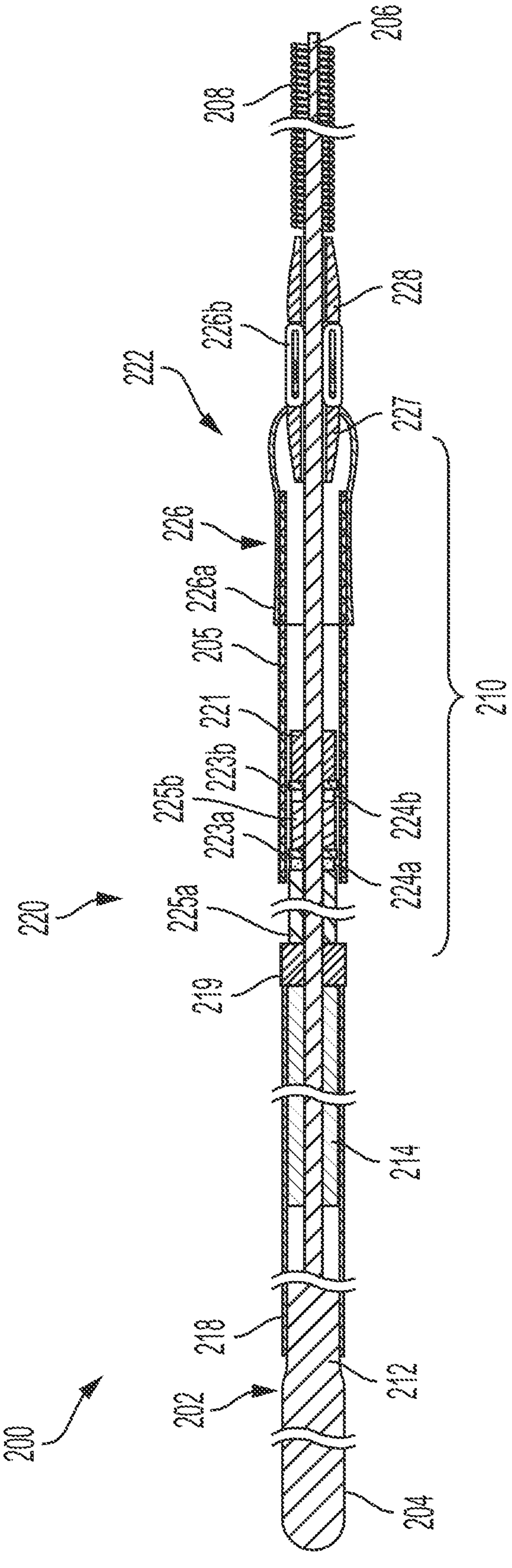
FIG. 2 is a side, cross-sectional view of a medical device delivery system in accordance with several embodiments of the present technology.

FIG. 2 illustrates a side cross-sectional view of a medical device delivery system 200 configured in accordance with several embodiments of the present technology. The delivery system 200 can be configured to carry a stent 205 (or other vascular implant or device) thereon to be advanced through a surrounding elongate shaft to a target site in a patient, similar to the operation described above with respect to FIG. 1. (The surrounding elongate shaft is omitted in FIG. 2 for clarity). The delivery system 200 can be advanced distally with respect to a distal end of the elongate shaft to expand or deploy the stent 205 at the target site.

The delivery system 200 can include and/or be used with any number of elongate shafts. In some embodiments, the elongate shaft is a catheter. For example, the catheter can optionally comprise any of the various lengths of the MARKSMAN™ catheter available from Medtronic Neurovascular of Irvine, California USA. The catheter can optionally comprise a microcatheter having an inner diameter of about 0.030 inches or less, and/or an outer diameter of 3 French or less near the distal region. Instead of or in addition to these specifications, the catheter can comprise a microcatheter which is configured to access the internal carotid artery, or another location within the neurovasculature distal of the internal carotid artery.

The delivery system 200 can comprise a core member or core assembly 202 configured to extend generally longitudinally through the lumen of an elongate shaft. The core member 202 can have a proximal region 204 and a distal region 206, which can optionally include a tip coil 208. The core member 202 can also comprise an intermediate portion 210 located between the proximal region 204 and the distal region 206. The intermediate portion 210 is the portion of the core member 202 onto or over which the stent 205 extends when the core member 202 is in the pre-deployment configuration as shown in FIG. 2.

The core member 202 can generally comprise any member(s) with sufficient flexibility and column strength to move a stent or other medical device through a surrounding elongate shaft. The core member 202 can therefore comprise a wire, tube (e.g., hypotube), braid, coil, or other suitable member(s), or a combination of wire(s), tube(s), braid(s), coil(s), etc. The embodiment of the core member 202 depicted in FIG. 2 is of multi-member construction, comprising a wire 212 with a tube 214 surrounding the wire 212 along at least a portion of its length. An outer layer 218, which can comprise a layer of lubricious material such as PTFE (polytetrafluoroethylene or TEFLON™) or other lubricious polymers, can cover some or all of the tube 214 and/or wire 212. The wire 212 may taper or vary in diameter along some or all of its length. The wire 212 may include one or more fluorosafe markers (not shown), and such marker(s) can be located on a portion of the wire 212 that is not covered by the outer layer 218 (e.g., proximal of the outer layer 218). This portion of the wire 212 marked by the marker(s), and/or proximal of any outer layer 218, can comprise a bare metal outer surface.

The core member 202 can further comprise a proximal coupling assembly 220 and/or a distal interface assembly 222 that can interconnect the stent 205 with the core member 202. The proximal coupling assembly 220 can comprise one or more engagement members 223*a*, 223*b* (collectively "engagement members 223") and/or one or more release members 224*a*, 224*b* (collectively "release members 224"). The release members 224 are configured to assume a first, compressed state when the coupling assembly 220 is positioned within the lumen of the surrounding elongate shaft so that the engagement members 223 may mechanically engage or interlock with the stent 205. In this manner, the proximal coupling assembly 220 cooperates with an overlying inner surface of a surrounding elongate shaft (not shown) to grip engage the stent 205 such that the proximal coupling assembly 220 can move the stent 205 along and within the elongate shaft, e.g., as the user pushes the core member 202 distally and/or pulls the core member proximally relative to the elongate shaft, resulting in a corresponding distal and/or proximal movement of the stent 205 within the elongate shaft lumen. As the stent 205 and coupling assembly 220 are advanced distally out of the surrounding elongate shaft lumen, the release members 224 are configured to radially expand to facilitate the stent 205 disengaging from the engagement members 223.

The proximal coupling assembly 220 can, in some embodiments, be similar to any of the versions or embodiments of the coupling assembly 120 described above with respect to FIG. 1. For example, the proximal coupling assembly 220 can include proximal and distal restraints 219, 221 that are fixed to the core member 202 (e.g., to the wire 212 thereof in the depicted embodiment) so as to be immovable relative to the core member 202, either in a longitudinal/sliding manner or a radial/rotational manner. The proximal coupling assembly 220 can also include a plurality of engagement members 223 and/or a plurality of release members 224, separated by one or more spacers 225. For example, the proximal coupling assembly 220 can include a first engagement member 223*a* and a first release member 224*a* separated from the proximal restraint 219 by a first spacer 225*a*, and a second engagement member 223*b* and a second release member 224*b* separated from the first engagement member 223*a* and the first release member 224*a* by a second spacer 225*b*.

The engagement members 223, the release members 224, and/or the spacers 225 can be coupled to (e.g., mounted on) the core member 202 so that the proximal coupling assembly 220 can rotate about the longitudinal axis of the core member 202 (e.g., of the intermediate portion 210), and/or move or slide longitudinally along the core member 202. In some embodiments, the proximal restraint 219 comprises a substantially cylindrical body with an outer diameter that is greater than or equal to an outer diameter of the first spacer 225*a*. The distal restraint 221 can taper in the distal direction down towards the core member 202. This tapering can reduce the risk of the distal restraint 221 contacting an inner surface of the overlying stent 205, particularly during navigation of tortuous vasculature, in which the system 200 can assume a highly curved configuration. In some embodiments, the distal restraint 221 can have an outside diameter or other radially outermost dimension that is smaller than the outside diameter or other radially outermost dimension of the overall proximal coupling assembly 220, so that distal restraint 221 will tend not to contact or apply radial force to the inner surface of the overlying stent 205.

In the proximal coupling assembly 220 shown in FIG. 2, the stent 205 can be moved distally or proximally within an overlying elongate shaft (not shown) via the proximal coupling assembly 220. In some embodiments, the stent 205 can be resheathed via the proximal coupling assembly 220 after partial deployment of the stent 205 from a distal opening of the elongate shaft, in a manner similar to that described above with respect to the coupling assembly 120 in FIG. 1.

The proximal coupling assembly 220 can be configured and function in a manner similar to the embodiment of the coupling assembly 120 depicted in FIG. 1. Specifically, the proximal restraint 219 can be made to function as a pushing element by appropriately sizing the outer diameter of the proximal restraint 219 and the length of the first spacer 225*a*, such that the distal face of the proximal restraint 219 abuts the proximal end or edge of the stent 205. When the proximal coupling element 220 is so arranged, the proximal restraint 219 can transmit at least some, or most or all, distally directed push force to the stent 205 during delivery, and the engagement member(s) 223 do not transmit any distally directed push force to the stent 205 during delivery (or transmit only a small portion of such force, or do so only intermittently). The engagement member(s) 223 can transmit proximally directed pull force to the stent 205 during retraction or resheathing, and the proximal restraint 219 can transmit no proximally directed pull force to the stent (or it may do so occasionally or intermittently, for example when a portion of the stent 205 becomes trapped between the outer edge of the proximal restraint 219 and the inner wall of the elongate shaft). Similar to the coupling assembly 120 shown in FIG. 1, the release members 224 can be configured to expand upon release from the lumen of the surrounding elongate shaft to facilitate expansion of the stent 205 and release of the engagement members 223 from the stent 205.

Although the proximal coupling assembly 220 can be configured in such a manner, with the proximal restraint 219 abutting the stent 205 so that the proximal restraint 219 can be used as a pushing element, in some embodiments, for example as shown in FIG. 2, the coupling assembly 220 may be configured such that the engagement members 223 are used for distal (delivery) and/or proximal (resheathing) movement of the stent 205, as described elsewhere herein.

Optionally, the proximal edge of the proximal coupling assembly 220 can be positioned just distal of the proximal edge of the stent 205 when in the delivery configuration. In some such embodiments, this enables the stent 205 to be re-sheathed when as little as a few millimeters of the stent remains in the elongate shaft. Therefore, with stents of typical length, resheathability of 75% or more can be provided (i.e. the stent can be re-sheathed when 75% or more of it has been deployed).

With continued reference to FIG. 2, the distal interface assembly 222 can comprise a distal engagement member 226 that can take the form of, for example, a distal device cover or distal stent cover (generically, a "distal cover"). The distal cover 226 can be configured to reduce friction between the stent 205 (e.g., a distal portion thereof) and the inner surface of a surrounding elongate shaft. For example, the distal cover 226 can be configured as a lubricious, flexible structure having a free first end or section 226*a* that can extend over at least a portion of the stent 205 and/or intermediate portion 267 of the core member 202, and a fixed second end or section 226*b* that can be coupled (directly or indirectly) to the core member 202. In some embodiments, the distal cover 226 is rotatably coupled to the core member 202.

The distal cover 226 can have a first (e.g., delivery) position, configuration, or orientation in which the distal cover can extend proximally relative to the distal tip 264, or proximally from the second section 226*b* or its (direct or indirect) attachment to the core member 202, and at least partially surround or cover a distal portion of the stent 205. The distal cover 226 can be movable from the first orientation to a second (e.g., resheathing) position, configuration, or orientation (not shown) in which the distal cover can be everted such that the first end 226*a* of the distal cover is positioned distally relative to the second end 226*b* of the distal cover 226 to enable the resheathing of the core member 202, either with the stent 205 carried thereby, or without the stent 205.

In some embodiments, one or both of the proximal and distal restraints 227, 228 can have an outside diameter or other radially outermost dimension that is smaller than the (e.g., pre-deployment) outside diameter or other radially outermost dimension of the distal cover 226, so that one or both of the restraints 227, 228 will tend not to bear against or contact the inner surface of the elongate shaft during operation of the core member 202. Alternatively, it can be preferable to make the outer diameters of the restraints 227 and 228 larger than the largest radial dimension of the pre-deployment distal cover 226, and/or make the outer diameter of the proximal restraint 227 larger than the outer diameter of the distal restraint 228. This configuration allows easy and smooth retrieval of the distal cover 226 and the restraints 227,228 back into the elongate shaft post stent deployment.

In embodiments of the core member 202 that employ both a rotatable proximal coupling assembly 220 and a rotatable distal cover 226, the stent 205 can be rotatable with respect to the core member 202 about the longitudinal axis thereof, by virtue of the rotatable connections of the proximal coupling assembly 220 and distal cover 226. In such embodiments, the stent 205, proximal coupling assembly 220 and distal cover 226 can rotate together in this manner about the core member 202. When the stent 205 can rotate about the core member 202, the core member 202 can be advanced more easily through tortuous vessels as the tendency of the vessels to twist the stent 205 and/or core member 202 is negated by the rotation of the stent 205, proximal coupling assembly 220, and distal cover 226 about the core member 202. In addition, the required push force or delivery force is reduced, as the user's input push force is not diverted into torsion of the stent 205 and/or core member 202. The tendency of a twisted stent 205 and/or core member 202 to untwist suddenly or "whip" upon exiting tortuosity or deployment of the stent 205, and the tendency of a twisted stent to resist expansion upon deployment, are also reduced or eliminated. Further, in some such embodiments of the core member 202, the user can "steer" the core member 202 via the tip coil 208, particularly if the coil 208 is bent at an angle in its unstressed configuration. Such a coil tip can be rotated about a longitudinal axis of the system 200 relative to the stent, coupling assembly 220 and/or distal cover 226 by rotating the distal region 206 of the core member 202. Thus the user can point the coil tip 208 in the desired direction of travel of the core member 202, and upon advancement of the core member the tip will guide the core member in the chosen direction.

Figure 3:
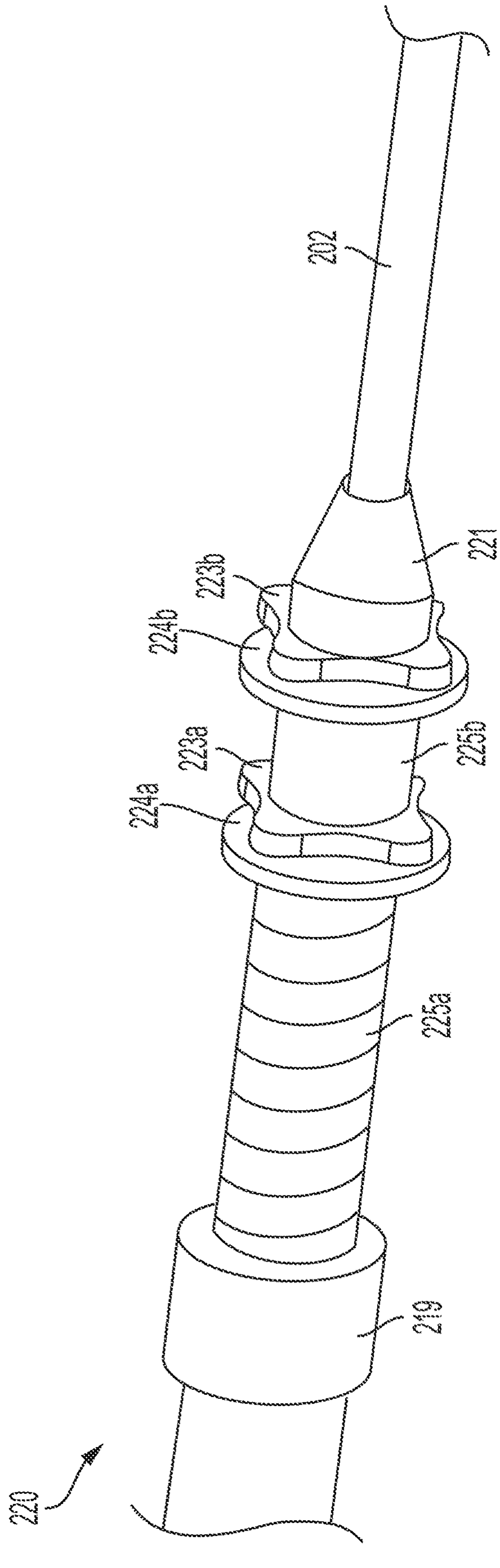
FIG. 3 is an enlarged perspective view of a coupling assembly having engagement members and release members in accordance with several embodiments of the present technology.
Figure 4B:
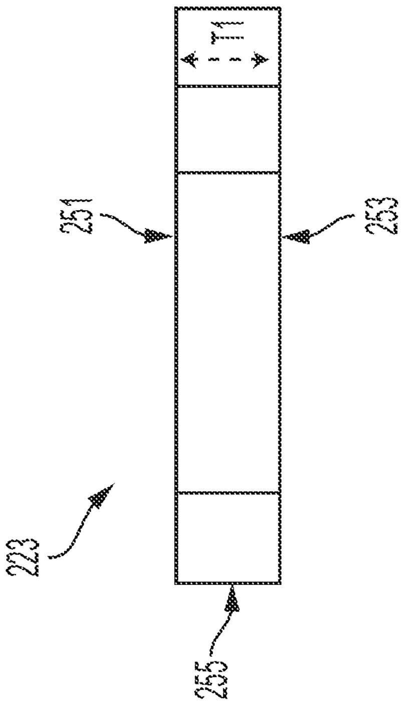
FIGS. 4A and 4B are side and top views, respectively, of an individual engagement member of the coupling assembly shown in FIG. 3.
Figure 4A:
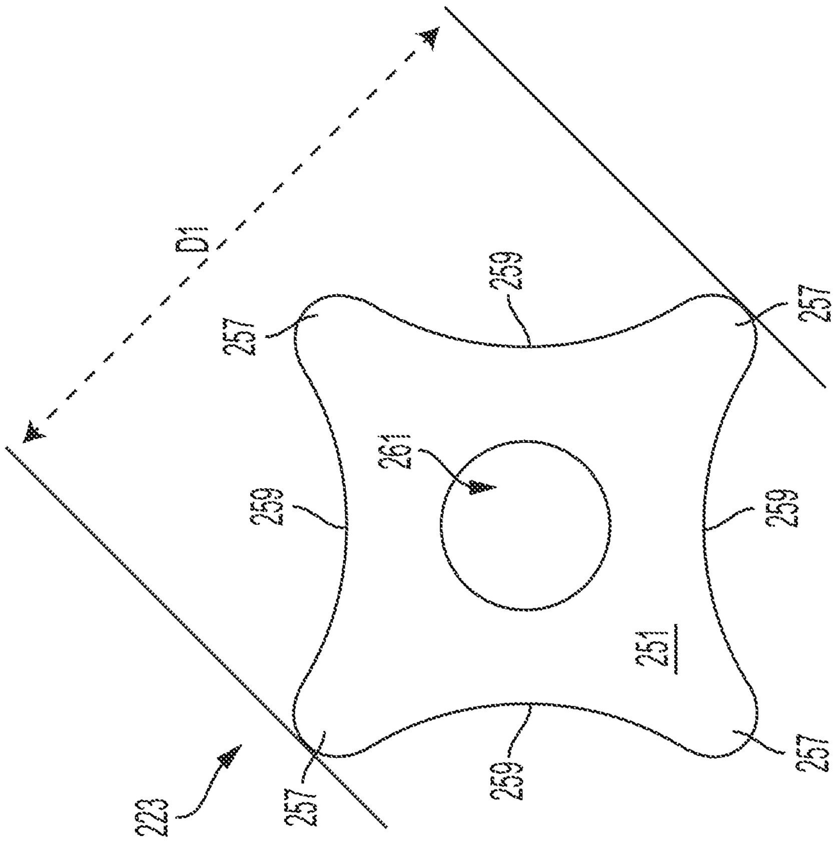
Figure 5B:
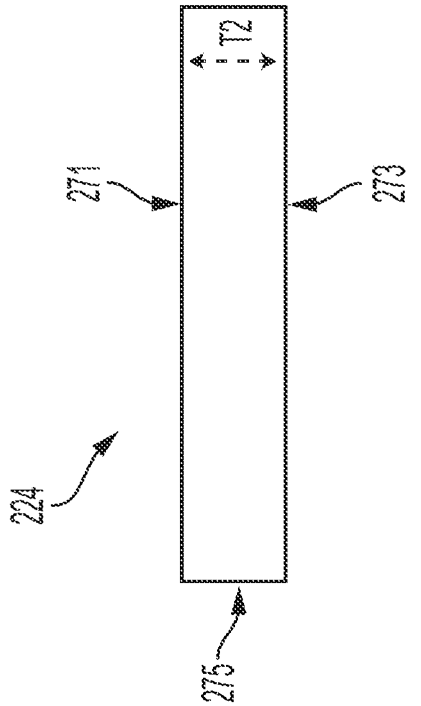
FIGS. 5A and 5B are side and top views, respectively, of an individual release member of the coupling assembly shown in FIG. 3.
Figure 5A:
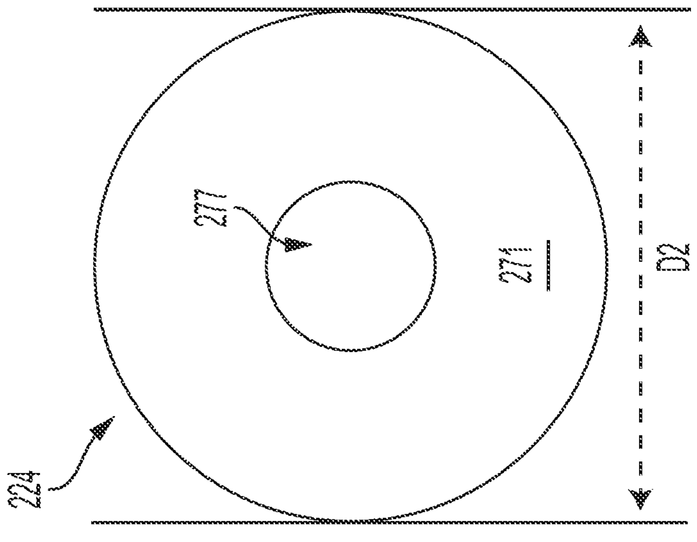

FIG. 3 is an enlarged perspective view of the embodiment of the coupling assembly 220 of the medical device delivery system 200 depicted in FIG. 2, FIGS. 4A and 4B are side and end views, respectively of one of the engagement members 223 of the coupling assembly 220, and FIGS. 5A and 5B are side and end views, respectively, or one of the release members 224 of the coupling assembly 220. With reference to FIGS. 3-5B together, the coupling assembly 220 can include first and second engagement members 223*a*, 223*b*, first and second release members 224*a*, 224*b*, and first and second spacers 225*a*, 225*b* mounted over the core member 202 and positioned between proximal and distal restraints 219, 221. The first engagement member 223*a* can be positioned adjacent to the first release member 224*a* and/or the second engagement member 223*b* can be positioned adjacent to the second release member 224*b*. For example, as shown in FIG. 3, the first engagement member 223*a* and the first release member 224*a* can be positioned adjacent to one another and can be separated from the proximal restraint 219 by the first spacer 225*a*, and/or the second engagement member 223*b* and the second release member 224*b* can be positioned adjacent to one another and separated from the first engagement member 223*a* and the first release member 224*a* by the second spacer 225*b*. Adjacent engagement members 223 and release members 224 can be positioned substantially in contact with one another (e.g., the first engagement member 223*a* can abut the first release member 224*a*, etc.). In some embodiments, the engagement members 223 can be longitudinally spaced apart from adjacent release members 224 (e.g., the first engagement member 223*a* is longitudinally spaced apart from the first release member 224*a*, the second engagement member 223*b* is longitudinally spaced apart from the second release member 224*b*, etc.). As shown in FIG. 3, the first release member 224*a* can be positioned proximal of the first engagement member 223*a* and/or the second release member 224*b* can be positioned proximal of the second engagement member 223*b*. In some embodiments, a release member 224 can be positioned distal of an adjacent engagement member 223. Although FIG. 3 depicts one release member 224 positioned adjacent to each engagement member 223, in some embodiments zero, one, two, or more release members 224 can be positioned adjacent to each engagement member 223. For example, one release member 224 can be positioned proximal of and adjacent to the engagement member 223 and one release member can be positioned distal of and adjacent to the same engagement member 223. In some embodiments, multiple release members 224 can be positioned adjacent to one another and/or multiple engagement members 223 can be positioned adjacent to one another.

As shown in FIGS. 4A and 4B, one or more of the engagement members 223 can have a plate-like or sprocket-like configuration with first and second end faces 251, 253 and a side surface 255 extending between the first and second end faces 251, 253. The engagement member 223 can include a plurality of radially extending projections 257 separated by recesses 259. In the illustrated embodiment, there are four projections 257 separated by four recesses 259. In various embodiments the number of projections can vary, for example two, three, four, five, six, seven, or more projections 257 separated by a corresponding number of recesses 259.

In some embodiments, the projections 257 include rounded edges and the recesses 259 include rounded depressions. During use of the delivery system 200, the rounded edges can prevent or limit scraping of the projections 257 against the inner wall of the overlying elongate shaft, which can reduce generation of particulates and damage to the elongate shaft. When the delivery system 200 is used with a braided stent, the recesses 259 can be sized to accommodate the thickness of braid wire crossings such that each projection 257 can extend at least partially into a pore of the stent 205 between the adjacent wire crossings and the wire crossings surrounding the pore can be at least partially received within the recesses 259 of the engagement member 223. In some embodiments, the projections 257 and/or the recesses 259 can assume other forms, for example with sharper or flatter peaks formed by the projections 257.

The projections 257 can each include an outermost contact region, characterized by a length, which is configured to contact (or otherwise engage with) an overlying stent. The contact region can include a central portion flanked by opposing shoulder portions extending between the central portion and opposing extensions. The extensions extend away from the contact region and towards corresponding recesses of the engagement member. The central portion can have a substantially planar outermost surface, which can be coplanar with the adjacent shoulder portions. However, the shoulder portions can have curved outer surfaces which join the central portion and the adjacent extensions. Together, the central portion and shoulder portions define the length of the contact region. In certain embodiments, it can be advantageous to increase the overall surface area of the contact region by increasing the length as compared to embodiments in which there is little or no central portion. The various embodiments of the contact region can generally comprise a flat or planar central region, and first and second shoulders on either side of the central region. The shoulders can be rounded in up to two directions (e.g., radially and/or axially).

Each engagement member 223 can include an opening or central aperture 261 configured to receive the core member 202 therethrough. The opening of the aperture 261 can be larger than the diameter of the core member 202 such that the engagement members 223 can rotate about the long axis of the core member 202. In some embodiments, the aperture 261 can be sufficiently larger than the diameter of the core member 202 to permit a degree of tilting of the engagement member 223 with respect to a longitudinal axis of the core member 202.

The engagement members 223 can be made to have a relatively thin and/or plate-like or sprocket-like configuration. Such a configuration can facilitate the formation of projections 257 that are small enough to fit inside the pores of the stent 205. Accordingly, the engagement members 223 may be characterized by a largest radial dimension or diameter D1 along the first and second end faces 251, 253, and a thickness T1 measured along the side surface 255. In some embodiments, the diameter D1 is at least five times greater than the thickness T1. In at least one embodiment, the thickness T1 is between approximately 25-200 microns, or 50-100 microns, for example, approximately 80 microns.

To effectively push or pull the stent 205 along a surrounding elongate shaft, the engagement members 223 can be made to be rigid (e.g., incompressible by the forces encountered in typical use of the delivery system). The rigidity of the engagement members 223 can be due to their material composition, their shape/construction, or both. In some embodiments, the engagement members 223 are made of metal (e.g., stainless steel, Nitinol, etc.) or rigid polymers (e.g., polyimide, PEEK), or both. In some embodiments, the engagement members 223 can be made of stainless steel and manufactured using laser cutting followed by electropolishing. For example, a plurality of engagement members can be laser-cut from a sheet of stainless steel having the desired thickness (e.g., approximately 100 microns thick). Electropolishing can further reduce the thickness of the resulting engagement members, for example from 100 microns to approximately 80 microns. In some embodiments, the engagement members can be manufactured using other techniques, for example injection molding, chemical etching, or machining. In some embodiments, even if the engagement member 223 is made of a rigid material, based on structural characteristics the engagement member itself may be non-rigid and at least partially compressible.

In various embodiments, the engagement members 223 of the coupling assembly 220 can take additional forms. For example, the number of projections 257, the contours of the projections 257 and recesses 259, the material selected, and dimensions can all vary to achieve desired operation of the coupling assembly 220. In some embodiments, the individual engagement members 223 of a given coupling assembly 220 can be substantially identical in shape, size, and construction. In some embodiments, the properties of the individual engagement members 223 can vary within a single coupling assembly 220, such as having different sizes, shapes, or material construction. For example, a single coupling assembly 220 can have a first engagement member **223*a* having a given number of projections 257, and a second engagement member 223*b* having a different number of projections 257**.

Depending on the particular construction of the overlying stent 205, in some embodiments the projections 257 of the engagement members 223 can be evenly radially spaced around the side surface 255 of the engagement members 233. In braided stents, the number of strands defines the number of available pores radially aligned along any particular longitudinal location of the stent. In some embodiments, aligning each projection 257 with a pore improves the strength with which the engagement member 223 interlocks with the overlying stent 205 as well as overall mechanical fit and compatibility. Accordingly, it can be advantageous to align the projections 257 with pores of the overlying stent 205. When the number of pores along a particular longitudinal location is evenly divisible by the number of projections 257 of the engagement member 223, the projections 257 may be evenly radially spaced.

In some embodiments, the number of projections 257 of the engagement member 233 and the number and/or location of pores defined by the overlying stent 205 can be such that even radial spacing of the projections 257 would be disadvantageous. For example, a braided stent with 48 wires (and 24 pores) can be used with an engagement member 233 that has 5 projections 257, in which case these projections 257 cannot be evenly spaced around the engagement member 233 and still each be aligned with pores of the stent 205. In these cases, it can be advantageous to provide an engagement member 233 with projections 257 that are unevenly spaced apart from one another around a circumference of the engagement member 233. Similarly, in the case of a laser-cut stent, the pores may not be evenly radially spaced around the circumference of the stent, and an engagement member 233 with unevenly radially spaced projections 257 can be useful with such a stent. The recesses 259 can be shaped and sized differently from one another such that the projections 257 are not evenly spaced around the periphery of the engagement member 223. This varied spacing can be achieved by varying the structure of the individual recesses. For example, each recess 259 can include a concave surface which curves inwardly between adjacent projections 257. Certain recesses 259 can have a larger surface area and/or a larger radius of curvature than other projections 257, thereby extending the radial spacing between adjacent projections 257. Particular angles between adjacent projections 257 can be varied within ranges such that each projection 257 is configured to project into or mechanically interlock with a pore of an overlying stent 205.

As shown in FIGS. 5A and 5B, one or more of the release members 224 can have first and second end faces 271, 273 and a sidewall 275 extending between the first and second end faces 271, 273. In some embodiments, for example as shown in FIGS. 5A and 5B, the sidewall 275 can be substantially annular such that the release member 224 is substantially disc-shaped. Still, other shaped release members 224 are possible.

Each release member 224 can include an opening or central aperture 277 configured to receive the core member 202 therethrough. The opening of the aperture 277 can be larger than the diameter of the core member 202 such that the release member 224 can rotate about the long axis of the core member 202. In some embodiments, the aperture 277 can be sufficiently larger than the diameter of the core member 202 to permit a degree of tilting of the release member 224 with respect to a longitudinal axis of the core member 202. As previously noted, a ratio of a diameter of the aperture 277 to a diameter of the core member 202 can be selected based on a desired stability, rotatability, and/or ease of assembly of the release member 224. In various embodiments, the ratio is greater than or equal to one (e.g., the diameter of the aperture 277 is at least as large as the diameter of the core member 202). For example, the ratio can be between about 1 and about 5, between about 2 and 4, between about 1 and about 4, between about 1 and about 3, or between about 1 and about 2. The ratio can be greater than about 1, greater than about 2, greater than about 3, greater than about 4, or greater than about 5. In some embodiments, the ratio is about 5, about 4, about 3, about 2, or about 1. In some embodiments, the ratio is less than 1 (e.g., the diameter of the aperture 277 is less than the diameter of the core member 202). For example, the ratio can be between about 1.0 and about 0.0, between about 0.9 and about 0.1, between about 0.8 and about 0.2, between about 0.7 and about 0.3, or between about 0.6 and about 0.4. The ratio can be less than about 1.0, less than about 0.9, less than about 0.8, less than about 0.7, less than about 0.6, less than about 0.5, less than about 0.4, less than about 0.3, less than about 0.2, or less than about 0.1. In some embodiments, the ratio is about 0.0, about 0.1, about 0.2, about 0.3, about 0.4, about 0.5, about 0.6, about 0.7, about 0.8, or about 0.9. The release member 224 can be positioned over the core member 202 via an interference fit to improve stability of the release member 224 on the core member 202. In some embodiments, an interference fit between the release member 224 and the core member 202 does not substantially inhibit or prevent rotatability of the release member 224 about the core member 202. In some embodiments, for example when the core member 202 has a diameter of 0.140 mm, a diameter of the aperture 277 is between about 0.000 mm and about 0.127 mm. For example, the diameter of the aperture can be about 0.051 mm.

As shown in FIGS. 5A and 5B, the release members 224 can be characterized by a largest radial dimension or diameter D2 along the first and second end faces 271, 273 and a thickness T2 measured along the sidewall 275. The thickness T2 can be between about 0.025 mm and about 1 mm. For example, the thickness T2 can be between about 0.05 mm and 0.150 mm. The thickness T2 can be uniform or can vary. As described herein, the release members 224 can be movable between a radially compressed configuration and a radially expanded configuration to control engagement of the engagement members 223 with the stent 205. As such, the diameter D2 of the release members 224 can vary based on the configuration of the release member 224. When the release member 224 is in the compressed configuration, the diameter D2 of the release member 224 can be smaller than the diameter D1 of the engagement members 223. When the release member 224 is in the expanded configuration, the diameter D2 of the release member 224 can be nearly as large as the diameter D1 of the engagement members 223 or at least as large as the diameter D1 of the engagement members 223 to prevent or limit the engagement members 223 from engaging the pores of the stent 205 when not constrained within the elongate shaft. In the expanded configuration, a ratio of the diameter D2 of the release member 224 to the diameter D1 of the engagement member 223 can be between about 0.85 to about 1.25, between about 0.90 to about 1.20, between about 0.95 to about 1.15, between about 1.00 to about 1.10, or between about 1.02 to about 1.04.

One or more of the release members 224 can be formed of a resilient material having elastic properties and/or a material having shape memory and/or superelastic properties. Accordingly, when the release member 224 is advanced out of the elongate shaft lumen, the release member 224 can expand from the compressed configuration to the expanded configuration. For example, the release member 224 can be formed from an elastomeric material (e.g., a silicone elastomer). In some embodiments, the release member is formed from an elastomeric material having a Shore A hardness of between about 20 and about 60, between about 25 and about 55, between about 30 and about 50, or between about 35 and about 45. Still, the release member 224 can be formed from other materials such as metal, other polymers, ceramics, etc.

The release member 224 can be manufactured using techniques such as, but not limited to, casting, molding (e.g., injection molding, etc.), 3D printing, cutting, deposition, extrusion, and/or another suitable technique. In some embodiments, the release member 224 is cut from a sheet or tube of material. For example, the release member 224 can be cut from a sheet of silicone or another suitable material as described herein. The sheet or tube of material can have a thickness corresponding to the desired thickness T2 of the release member 224. Additionally or alternatively, the thickness T2 of the release member 224 can be modified after the release member 224 are cut from the sheet or tube of material. The release member 224 can be cut from the sheet or tube of material via laser cutting, milling, chemical etching, water jetting, punching, stamping, or other suitable technique. The aperture 277 can be formed in the release member 224 by cutting the release member 244 as described herein. In some embodiments, the aperture 277 is formed by creating an opening in the release member 224 using a wire or the core member 202.

In some embodiments, the release member 224 is formed by extruding the desired material into an elongate member having an outer diameter corresponding to a desired largest radial dimension of the release member 224. The elongate member can be cut along a longitudinal dimension of the elongate member to form the release member 224 such that the release member 224 has the desired thickness T2. The material can be extruded such that the elongate member is tubular and has an aperture corresponding to the aperture 277 of the release member 244 as disclosed herein. In some embodiments, the material is extruded such that the elongate member does not have an aperture. In some embodiments, an aperture is formed in the elongate member after the elongate member has been extruded. In any case, the release member 224 can be modified after being cut from the elongate member to create or modify the aperture 277.

In the assembled delivery system 200, the first and second end faces 251, 253 of the engagement members 223 and/or the first and second end faces 271, 273 of the release members 224 can be oriented and maintained substantially orthogonal to a long axis of the core member 202 (or the engagement members and/or release members can be configured to tilt to a desired degree, as discussed elsewhere herein). This can be achieved by configuring the spacers 225 with distal and proximal end faces that are orthogonal to the longitudinal axis of each spacer 225 (and/or to the core member 202), configuring the release members 224 with distal and proximal end faces that are parallel to the distal and proximal end faces of the spacers 225, and/or minimizing the amount of longitudinal movement space (or "play") among the engagement members 223, the release members 224, and spacers 225 of the coupling assembly 220. This can also be achieved by configuring the aperture 277 to have a diameter that is smaller than a diameter of the core member 202, as described herein.

Figure 6A:
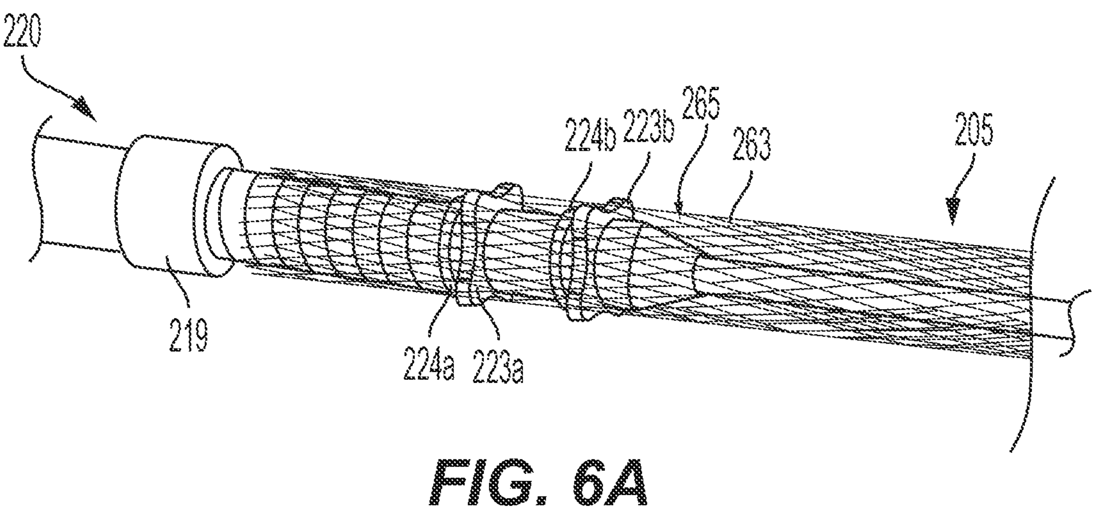
FIG. 6A is an enlarged perspective view of the coupling assembly of FIG. 3 with an overlying medical device engaged with the engagement members.
Figure 6B:
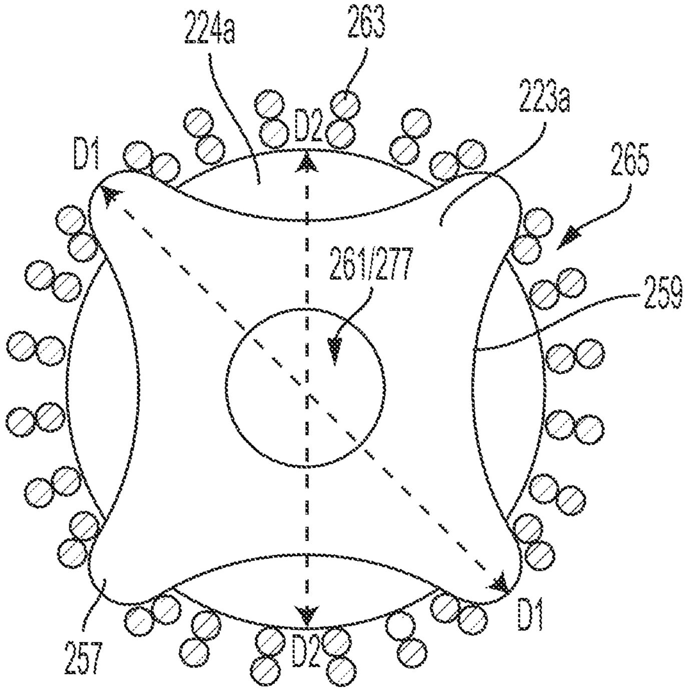
FIG. 6B is a schematic cross-sectional view of an engagement member, a release member, and the medical device of FIG. 6A.

FIGS. 6A and 6B are perspective and cross-sectional views, respectively, of the coupling assembly 220 with the release members 224 in a compressed configuration and an overlying stent 205 engaged with the engagement members 223. The depicted stent 205 is braided (although other types of stent, as disclosed elsewhere herein may be used) and includes a mesh 263 forming a plurality of pores 265 which are bounded by filaments, wires or struts and separated by points where the filaments, wires or struts cross (e.g., in the case of a braided or woven device) or intersect (e.g., in the case of a laser-cut device).

In some embodiments, the release members 224 assume the compressed configuration, and/or the overlying stent 205 is engaged with the engagement members 223, when the coupling assembly 220 and stent 205 are positioned within a lumen of an elongate shaft (not shown for clarity). Radial compression of the stent 205 by the elongate shaft can cause the release members 224 to assume the compressed configuration. Additionally or alternatively, the coupling assembly 220 can include one or more actuation elements (e.g., springs, coils, braids, balloons, vacuum pumps, etc.) configured to facilitate compressing the release members 224. As shown in FIGS. 6A and 6B, when one of the release members 224 is in the compressed configuration, a largest radial dimension (e.g., diameter D2) of the release member 224 can be less than a largest radial dimension (e.g., diameter D1) of one or more of the engagement members 223 (e.g., an adjacent engagement member 223). Consequently, the one or more engagement members 223 can mechanically interlock with or engage the stent 205 such that one or more of the projections 257 is at least partially received within a pore 265 of the stent 205 between adjacent wire crossings and the wire crossings surrounding the pore 265 can be at least partially received within the recesses 259.

The interaction between the projections 257 and the pores 265 can produce a mechanical interlock between the engagement member 223 and the pores 265. This is in contrast to a conventional compressible pad that resiliently pushes against the stent as a whole, including the wire crossings. In at least some embodiments, the mechanical interlock provided by the engagement members 223 secures the stent 205 without pressing against the wire crossings of the stent 205. In some embodiments, the engagement members 223 are configured to secure a range of different stent sizes within a given elongate shaft size (e.g., within a 0.017", 0.021" or 0.027" elongate shaft (inside diameter)).

In some embodiments, the coupling assembly 220 can be configured to engage only a proximal portion (e.g., the proximalmost 5%, the proximalmost 10%, the proximalmost 20%, only a proximal half, etc.) of the stent 205. In various embodiments, coupling assembly 220 can engage the stent 205 along substantially its entire length.

In some embodiments, the first engagement member **223*a* can engage with a proximal portion of the stent 205, for example at a position less than 5 pores or pore lengths away from a proximal end of the stent, or less than 3 pores or pore lengths away from the proximal end of the stent 205, etc. The spacers 225 can be configured with a length and/or the release members 224 can be configured with a thickness such that the projections 257 of adjacent engagement members 223 (e.g., the first engagement member 223*a* and adjacent second engagement member 223*b*) are spaced apart longitudinally by a distance that is substantially equal to the "pore length" (or "pore pitch") of the stent 205 (defined herein as the longitudinal distance between the centers of longitudinally adjacent and non-overlapping pores 265 when the stent is in the compressed configuration wherein the outer diameter of the stent is equal to the inner diameter of the elongate shaft) or, in some embodiments, a whole-number multiple of the pore length of the stent 205. For example, in some embodiments, the first and second engagement members 223*a* and 223*b* are spaced apart by between about 1-3 times the pore length of the stent 205 when the stent is at the inner diameter of the elongate shaft. Accordingly, each projection 257 can extend into and engage one of the pores 265 of the stent 205**.

Projections 257 of the engagement member 223 can engage individual pores 265 of the stent 205. In some embodiments, adjacent engagement members 223 engage longitudinally adjacent pores 265 of the stent 205. As used herein, "longitudinally adjacent" means that there i s not an intervening pore in the longitudinal direction between the two pores. Longitudinally adjacent pores, however, can be non-adjacent radially, e.g., a first pore located at the "twelve o'clock" position on the circumference of the stent can be longitudinally adjacent to a second pore located at the "six o'clock" position on the circumference of the stent (or at any point on the circumference in between) if, in the longitudinal direction, there is no intervening pore between the two. In some embodiments, adjacent engagement members 223 engage pores 265 which are not longitudinally adjacent but are spaced apart longitudinally by one or more intervening pores 265. Therefore, the first and second engagement members 223*a* and 223*b* can be spaced apart from one another by a longitudinal distance corresponding to the pore pitch of the stent 205, or by a longitudinal distance corresponding to a whole number multiple of the pore pitch.

In some embodiments, the longitudinal spacing between the first and second engagement members 223*a* and 223*b* can be slightly less than the pore length (e.g., 50% less, 40% less, 30% less, 20% less, 10% less, or 5% less than the pore length, etc.), or slightly less than a whole number multiple of the pore length (e.g., less by a decrement equal to 50%, 40%, 30%, 20%, 10%, or 5% of a single pore length, etc.). This slightly smaller spacing between the first and second engagement members 223*a* and 223*b* can provide improved grip on the stent 205 by minimizing the longitudinal "play" between the projections 257 of the first and second engagement members 223*a* and 223*b* and the wire crossing(s) or intersection point(s) positioned between the engagement members. As a result, a longitudinal movement of the core member 202 causes a corresponding longitudinal movement of the stent 205 with minimal delay and high precision. For example, a proximal movement of the core member 202 (and/or the engagement member(s) 223 carried thereby) causes a proximal movement of the stent 205, with the engagement member(s) 223 moving no more than a first lag distance relative to the stent 205 before initiating proximal movement of the stent 205. The first lag distance can be more than 40% of the pore length of the stent 205, or no more than 33%, or no more than 25%, or no more than 20%, or no more than 15%, or no more than 10%, or no more than 5% of the pore length. Instead of or in addition to such a first pore length, a distal movement of the core member 202 (and/or the engagement member(s) 223 carried thereby) causes a distal movement of the stent 205, with the engagement member(s) 223 moving no more than a second lag distance relative to the stent 205 before initiating distal movement of the stent 205. The second lag distance can be more than 40% of the pore length of the stent 205, or no more than 33%, or no more than 25%, or no more than 20%, or no more than 15%, or no more than 10%, or no more than 5% of the pore length.

To deliver the stent 205 to a treatment site within a patient, the core member 202 can be advanced distally within the elongate shaft (or the elongate shaft retracted over the core member) so that the stent 205 extends out of the elongate shaft and radially expands. Moreover, as the core member 202 is advanced relative to the elongate shaft, the release members 224 can be configured to expand to facilitate expansion of the stent 205. For example, the release members 224 can be formed of a resilient (e.g., compressible and self-expanding) material such that the release members 224 expand once positioned distally of the lumen of the elongate shaft.

Figure 7A:
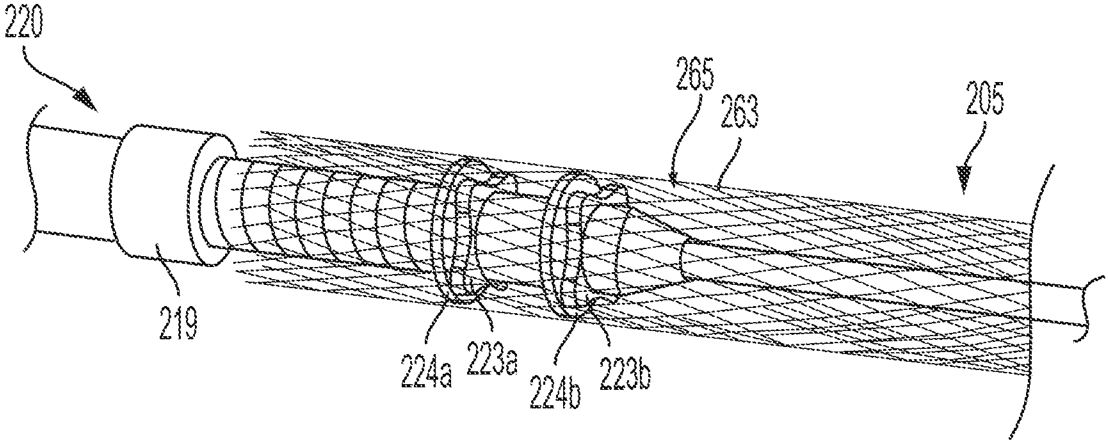
FIG. 7A is an enlarged perspective view of the coupling assembly of FIG. 3 with an overlying medical device expanded and disengaged from the engagement members.
Figure 7B:
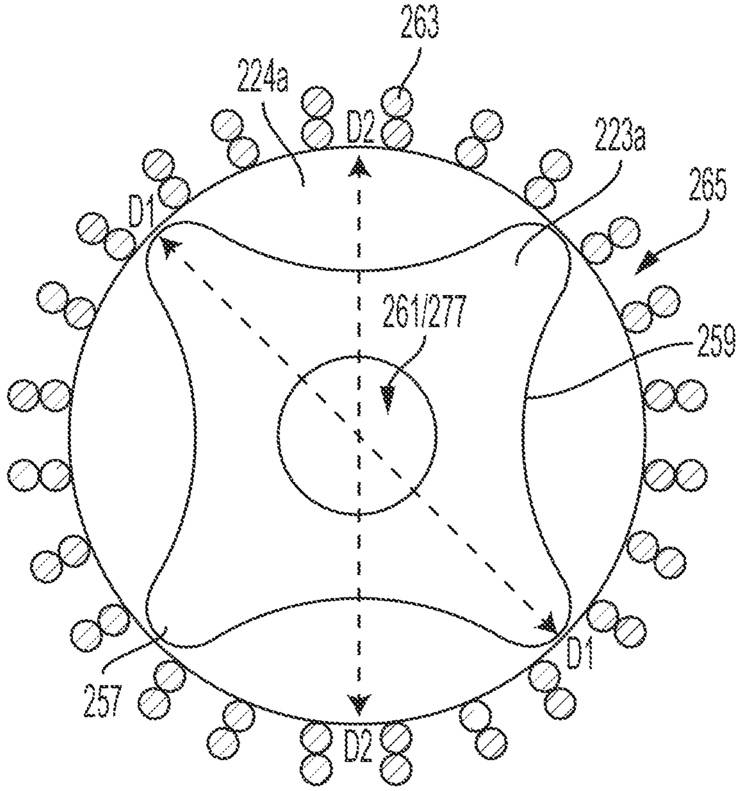
FIG. 7B is a schematic cross-sectional view of an engagement member, a release member, and the medical device of FIG. 7A.

FIGS. 7A and 7B are perspective and cross-sectional views, respectively, of the coupling assembly 220 with the release members 224 and the overlying stent 205 in an expanded configuration. In some embodiments, a radially largest dimension (e.g., a diameter) of the stent 205 when the stent 205 is in the expanded configuration is greater than the radially largest dimension of the stent 205 when the stent is in the compressed configuration. For example, the radially largest dimension of the stent 205 in the expanded configuration can be at least 2 times greater, at least 3 times greater, at least 4 times greater, at least 5 times greater, at least 6 times greater, at least 7 times greater, at least 8 times greater, at least 9 times greater, or at least 10 times greater than the radially largest dimension of the stent 205 in the compressed configuration. In some embodiments, the radially largest dimension of the stent 205 in the expanded configuration is between about 2 to about 10 times greater than the radially largest dimension of the stent 205 in the compressed configuration, between about 3 to about 9 times greater than the radially largest dimension of the stent 205 in the compressed configuration, between about 4 to about 8 times greater than the radially largest dimension of the stent 205 in the compressed configuration, or between about 5 to about 7 times greater than the radially largest dimension of the stent 205 in the compressed configuration. The release members 224 can be configured to facilitate expansion and/or release of the stent 205 by preventing the projections 257 of the engagement members 223 from engaging the stent 205 when the stent 205 is not positioned within the elongate shaft and/or by applying a radially outwardly directed force to the stent 205. For example, as shown in FIGS. 7A and 7B, when the release members 224 are in the expanded configuration, a radially largest dimension (e.g., diameter D2) of the release members 224 can be greater than (or no smaller than) a radially largest dimension (e.g., diameter D1) of the engagement members 223. Accordingly, the release members 224 can be configured to obstruct or block the projections 257 of the engagement member 223 to prevent the stent 205 from engaging or remaining engaged with the projections 257 when the stent 205 is not constrained within the elongate shaft. In some embodiments, the release members 224 can be configured to apply a force to the stent 205 to facilitate expansion of the stent 205. For example, if a portion of the stent 205 has not disengaged from the projections 257 of the engagement member 223, as the release member 224 expands the release member 224 can apply a radially outwardly directed force to push the portion of the stent 205 radially outward and/or away from the projections 257 of the engagement member 223. Additionally or alternatively, in the expanded configuration the release member 224 can prevent the stent 205 from inadvertently reengaging with the projections 257 of the engagement member 223. As described herein, the release members 224 can be configured to self-expand upon release from the elongate shaft. In some embodiments, the coupling assembly 220 comprises an actuation element (e.g., springs, balloons, hooks, pull-wires, coils, etc.) configured to facilitate expansion of release members 224. In some embodiments, the release members 224 themselves comprise such actuation elements.

Note that various components of the delivery system 200 of FIGS. 2-7B can be incorporated into the delivery system 100 of FIG. 1, and vice versa. For example, any of the disclosed embodiments of the coupling assembly 220 can be employed as the coupling assembly 120 of the delivery system 100. Similarly, any of the embodiments of the engagement members 223 can be employed as the engagement member(s) 123 of the delivery system 100, any of the embodiments of the release members 224 can be employed as the release member(s) 124 of the delivery system 100, and/or any of the embodiments of the spacers 225 can be employed as the spacer(s) 125 of the delivery system 100. Although many embodiments discussed herein include two engagement members 223 and two release members 224, in some embodiments the delivery system 200 can include three, four, or more engagement members and/or release members. The coupling assembly 220 may also include additional spacers. The spacing of such additional engagement members and/or release members can be regular or irregular. For example, in one embodiment a third engagement member can be provided at a position configured to engage a distal region of the overlying stent, while the first and second engagement members engage only a proximal region of the overlying stent. A third release member may be positioned adjacent to and/or proximal of the third engagement member.

Figure 8:
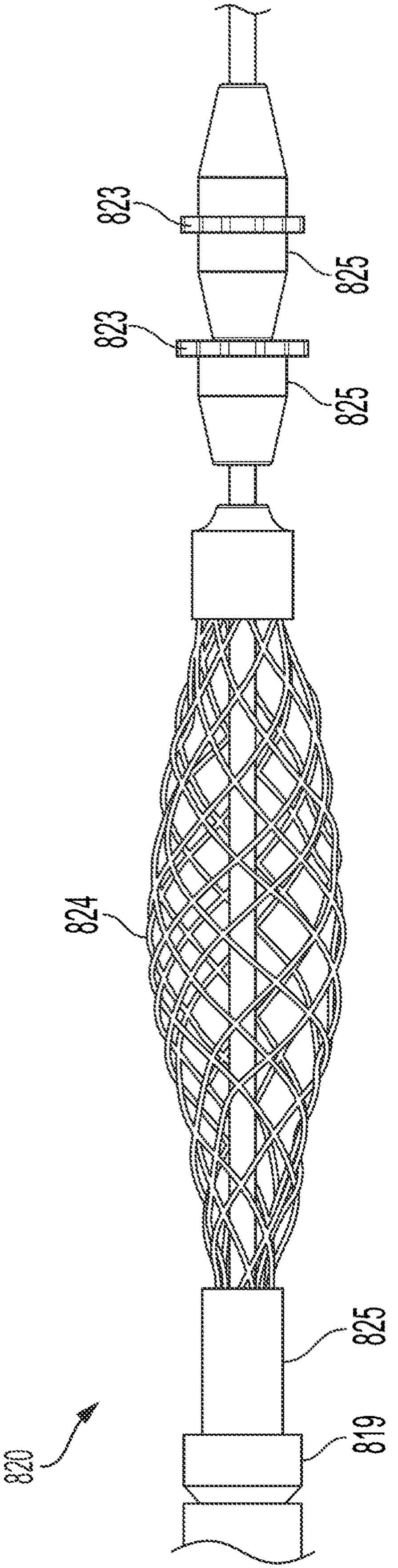
FIG. 8 depicts a coupling assembly in accordance with several embodiments of the present technology.

Although FIGS. 1-7 depict disc-shaped, resilient release members, in some embodiments the release members comprise other forms. For example, FIG. 8 shows one such embodiment of a coupling assembly 820. As shown in FIG. 8, the release member 824 can comprise a braid configured to be positioned between a proximal restraint 819 and a proximal engagement member 823 of the coupling assembly 820. The braid can be configured to expand to apply a radial force to a stent to facilitate expansion of the stent during delivery. The braid can be self-expanding and/or the coupling assembly 820 can include one or more additional elements configured to expand the braid (e.g., balloons, pull wires, etc.). The release member 824 can comprise any suitable member configured to apply a force to the stent and/or to disengage the stent from the engagement members 823. Such suitable members include, but are not limited to, radially expandable tubes, radially expanding struts or sets of struts as may be implemented in the form of a tube such as a laser-cut tube, balloons, springs, coils, braids, wires, etc. In some embodiments the shape, position, and/or configuration of the engagement members, the release members, and/or the spacers can be selected to facilitate expansion of the stent. For example, as shown in FIG. 8, the coupling assembly 820 can include spacers 825 that taper in a distal and/or proximal direction to reduce unintentional engagement between the stent and the engagement members 823. Additionally or alternatively, the number, spacing, and/or shape of the projections of the engagement members 823 can be selected to reduce the likelihood of unintentional engagement between the stent and the engagement members 823 during delivery of the stent.

Conclusion

Although many of the embodiments are described with respect to devices, systems, and methods for delivery of stents, tubular implants such as filters, shunts or stent-grafts and other medical devices, other applications and other embodiments in addition to those described herein are within the scope of the present technology, and can be employed in any of the embodiments of systems disclosed herein, in place of a stent as is typically disclosed. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-8.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A medical device delivery system comprising:

a core member configured for advancement within a corporeal lumen; and a coupling assembly positioned about the core member, the coupling assembly comprising:

an engagement member positioned about the core member, the engagement member including an outer portion having one or more projections separated by recesses along a circumferential direction, wherein the projections define an outer diameter of the engagement member and are configured to extend into pores of an overlying medical device; and a disc-shaped resilient member positioned about the core member, wherein the resilient member is movable between a first state in which an outer diameter of the resilient member is smaller than the outer diameter of the engagement member and a second state in which the outer diameter of the resilient member is greater than the outer diameter of the engagement member, such that in the second state the resilient member physically blocks the projections of the engagement member from extending into the pores of the overlying medical device.

2. The system of claim 1, further comprising a tubular stent having a substantially cylindrical inner wall and extending along the core member such that, when the resilient member is in the first state, the projections of the engagement member extend into one or more pores of the stent along the inner wall and, when the resilient member is in the second state, the resilient member prevents the projections from extending into the one or more pores of the stent along the inner wall.

3. The system of claim 1, further comprising an elongate tube defining a lumen therethrough, wherein the coupling assembly is configured to be positioned within the lumen of the elongate tube such that the resilient member assumes the first state.

4. The system of claim 3, wherein the coupling assembly is configured to be advanced through the lumen of the elongate tube such that the resilient member assumes the second state after exiting the lumen.

5. The system of claim 1, wherein the resilient member is positioned adjacent to and proximal of the engagement member.

6. The system of claim 1, wherein the resilient member abuts the engagement member.

7. The system of claim 1, wherein the engagement member is a first engagement member and the resilient member is a first resilient member, the coupling assembly further comprising a second engagement member positioned about the core member and a second resilient member positioned about the core member.

8. The system of claim 7, wherein the first resilient member is positioned proximally of the first engagement member and the second resilient member is positioned proximally of the second engagement member.

9. The system of claim 1, wherein the resilient member comprises an elastomeric material with a Shore A hardness of at least 20.

10. The system of claim 1, wherein the outer diameter of the engagement member is greater than a thickness of the engagement member.

11. A medical device delivery system comprising:

a core member configured for advancement through a lumen of an elongate tube;

a coupling assembly positioned about the core member, the coupling assembly comprising:

an engagement member positioned about the core member, the engagement member including an outer surface having one or more projections; and a release member positioned about the core member adjacent to the engagement member; and a tubular medical device having a substantially cylindrical inner surface and extending along the core member over the coupling assembly, the medical device having pores, wherein the medical device and the coupling assembly are configured to be positioned within a lumen of an elongate tube such that the release member is compressed and contacts the inner surface of the medical device about a circumference of the medical device and the one or more projections extend through one or more pores of the medical device along the inner surface, and wherein the core member is configured to be distally advanced within the lumen of the elongate tube such that, when the release member and the engagement member are positioned out of the lumen of the elongate tube, the release member and at least a portion of the medical device radially expand, and wherein upon said radial expansion the outer diameter of the release member is greater than an outer diameter of the engagement member, and the release member thereby physically blocks the one or more projections from extending into the one or more pores of the medical device.

12. The system of claim 11, wherein, when the release member radially expands, the release member applies a radial force to the medical device to separate the medical device from the one or more projections.

13. The system of claim 11, wherein, when the release member is compressed, an outer diameter of the release member is smaller than an outer diameter of the engagement member.

14. The system of claim 11, wherein the release member comprises a resilient material.

15. The system of claim 11, wherein the outer diameter of the engagement member is greater than a thickness of the engagement member.

16. A medical device delivery system comprising:

a core member; and a coupling assembly carried by the core member, the coupling assembly comprising:

an engagement member positioned about the core member, the engagement member including an outer surface having one or more projections configured to extend into pores of a medical device extending along the core member; and a disc-shaped expandable element located on the core member at a position longitudinally adjacent to the engagement member, the expandable element having a compressed configuration and an expanded configuration, wherein, when the expandable element is in the compressed configuration, the one or more projections extend into the pores of the medical device, and wherein expansion of the expandable element from the compressed configuration to the expanded configuration causes the disc-shaped expandable element to physically block the one or more projections from extending into the pores of the medical device, thereby causing the medical device to disengage from the projections, wherein, when the expandable element is in the compressed configuration, a largest radial dimension of the expandable element is smaller than a largest radial dimension of the engagement member and, when the expandable element is in the expanded configuration, the largest radial dimension of the expandable element is greater than the largest radial dimension of the engagement member.

17. The system of claim 16, wherein expansion of the expandable element causes the expandable element to apply a radially outwardly directed force to the medical device to cause the medical device to disengage from the projections.

18. The system of claim 16, further comprising an elongate tube having a lumen configured to receive the core member, the medical device, and the coupling assembly therethrough.

19. The system of claim 18, wherein, when the expandable element is positioned within the lumen of the elongate tube, the expandable element assumes the compressed configuration and, when the expandable element is advanced out of the lumen of the elongate tube, the expandable element assumes the expanded configuration.

20. The system of claim 16, wherein the expandable element comprises an elastomeric disc.

21. The system of claim 16, further comprising the medical device extending along the core member.

22. The system of claim 16, wherein an outer diameter of the engagement member is greater than a thickness of the engagement member.

* * * * *